US011510575B2

(12) United States Patent
Irisawa

(10) Patent No.: US 11,510,575 B2
(45) Date of Patent: Nov. 29, 2022

(54) PHOTOACOUSTIC IMAGE GENERATING DEVICE AND INSERTION OBJECT

(71) Applicant: FUJIFILM CORPORATION, Tokyo (JP)

(72) Inventor: Kaku Irisawa, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 254 days.

(21) Appl. No.: 16/855,105

(22) Filed: Apr. 22, 2020

(65) Prior Publication Data

US 2020/0245872 A1 Aug. 6, 2020

Related U.S. Application Data

(60) Division of application No. 14/755,766, filed on Jun. 30, 2015, now abandoned, which is a continuation of
(Continued)

(30) Foreign Application Priority Data

| Jan. 9, 2013 | (JP) | ................................. 2013-001519 |
| Jul. 18, 2013 | (JP) | ................................. 2013-149497 |
| Nov. 29, 2013 | (JP) | ................................. 2013-247739 |

(51) Int. Cl.
*A61B 5/00* (2006.01)
*A61B 18/14* (2006.01)
(Continued)

(52) U.S. Cl.
CPC .............. *A61B 5/0095* (2013.01); *A61B 5/06* (2013.01); *A61B 5/6851* (2013.01);
(Continued)

(58) Field of Classification Search
None
See application file for complete search history.

(56) References Cited

U.S. PATENT DOCUMENTS

| 5,158,088 A | 10/1992 | Nelson et al. |
| 5,402,792 A | 4/1995 | Kimura |

(Continued)

FOREIGN PATENT DOCUMENTS

| CN | 101636668 A | 1/2010 |
| CN | 102240213 A | 11/2011 |

(Continued)

OTHER PUBLICATIONS

International Search Report, issued in PCT/JP2013/082617, dated Jan. 7, 2014.

(Continued)

*Primary Examiner* — Katherine L Fernandez
(74) *Attorney, Agent, or Firm* — Birch, Stewart, Kolasch & Birch, LLP

(57) ABSTRACT

Even when an insertion object is inserted to a deep position of a subject or even when the insertion object is inserted into the subject at an angle close to a right angle, it is possible to confirm the position of the insertion object in a photoacoustic image. The insertion object is, for example, a hollow puncture needle 15 that includes an opening at a tip thereof. The puncture needle 15 includes a light guide member 152 that guides light emitted from a first light source to the vicinity of the opening, and a light emitting portion 153 that is provided in the vicinity of the opening and emits the light. First photoacoustic waves, which are caused by the light emitted from the light emitting portion 153, are generated in the puncture needle 15. A first photoacoustic image is generated on the basis of the first photoacoustic waves.

5 Claims, 33 Drawing Sheets

Related U.S. Application Data application No. PCT/JP2013/082617, filed on Dec. 4, 2013.

(51) Int. Cl.

| | | |
|---|---|---|
| *A61B 5/06* | (2006.01) | |
| *A61B 17/34* | (2006.01) | |
| *A61B 10/02* | (2006.01) | |
| *A61B 90/13* | (2016.01) | |
| *A61B 8/12* | (2006.01) | |
| *A61B 8/00* | (2006.01) | |
| *A61B 18/00* | (2006.01) | |

(52) U.S. Cl.
CPC .............. *A61B 5/6852* (2013.01); *A61B 8/12* (2013.01); *A61B 8/4281* (2013.01); *A61B 10/02* (2013.01); *A61B 10/0283* (2013.01); *A61B 17/3403* (2013.01); *A61B 18/1477* (2013.01); *A61B 90/13* (2016.02); *A61B 5/061* (2013.01); *A61B 5/6848* (2013.01); *A61B 2017/3413* (2013.01); *A61B 2018/00595* (2013.01)

(56) References Cited

U.S. PATENT DOCUMENTS

| | | | |
|---|---|---|---|
| 5,623,940 | A | 4/1997 | Daikuzono |
| 6,053,871 | A | 4/2000 | Cockburn |
| 9,468,500 | B2 | 10/2016 | Zhou |
| 2002/0058890 | A1 | 5/2002 | Visuri et al. |
| 2003/0093007 | A1 | 5/2003 | Wood |
| 2004/0067000 | A1 | 4/2004 | Bates et al. |
| 2004/0131299 | A1* | 7/2004 | Adoram ............... A61B 8/0841 385/12 |
| 2006/0241572 | A1 | 10/2006 | Zhou |
| 2008/0082045 | A1* | 4/2008 | Goldfarb ............ G02B 23/2469 604/96.01 |
| 2008/0108867 | A1 | 5/2008 | Zhou |
| 2010/0174197 | A1 | 7/2010 | Nakajima et al. |
| 2010/0249570 | A1* | 9/2010 | Carson ............... G01N 29/2418 600/407 |
| 2011/0251475 | A1 | 10/2011 | Tokita et al. |
| 2012/0253180 | A1 | 10/2012 | Emelianov et al. |
| 2012/0253200 | A1 | 10/2012 | Stolka et al. |
| 2013/0168532 | A1 | 7/2013 | Schmid et al. |
| 2013/0190591 | A1 | 7/2013 | Hirson et al. |
| 2014/0155739 | A1* | 6/2014 | Manohar ............. A61B 5/6848 600/424 |
| 2014/0187970 | A1* | 7/2014 | Suter .................... A61B 5/0084 600/478 |

FOREIGN PATENT DOCUMENTS

| | | | |
|---|---|---|---|
| CN | 102256537 | A | 11/2011 |
| CN | 102743191 | A | 10/2012 |
| JP | 57-40632 | A | 3/1982 |
| JP | 3-10255 | U | 1/1991 |
| JP | 6-43242 | A | 2/1994 |
| JP | 2001-517109 | A | 10/2001 |
| JP | 2003-299657 | A | 10/2003 |
| JP | 2009-31262 | A | 2/2009 |
| WO | WO 2011/137385 | A1 | 11/2011 |
| WO | WO 2012/189178 | A1 | 12/2012 |

OTHER PUBLICATIONS

Written Opinion of the International Searching Authority issued in PCT/JP2013/082617, dated Jan. 7, 2014.
Chinese Office Action and Search Report dated Jan. 25, 2016, for Chinese Application No. 201380069419.6 with an English translation of the Office Action.
Chinese Office Action and Search Report for Chinese Application No. 201710446982.0, dated Oct. 9, 2019, with English translation.
Chinese Office Action, dated Feb. 28, 2017, for Chinese Application No. 201380069419.6, with an English translation.
Chinese Office Action, dated Aug. 15, 2016, for Chinese Application No. 201380069419.6, along with an English translation.
European Office Action, dated Sep. 15, 2016, for European Application No. 13870517.3.
Extended European Search Report, dated Dec. 3, 2015, for European Application No. 13870517.3.
Extended European Search Report, dated May 9, 2018, for European Application No. 17205294.6.
Japanese Office Action dated Aug. 30, 2016, for Japanese Application No. 2015-192536 with the English translation.
Japanese Office Action dated Aug. 30, 2016, for Japanese Application No. 2015-192537 with the English translation.
U.S. Office Action for U.S. Appl. No. 14/755,766, dated Apr. 14, 2017.
U.S. Office Action for U.S. Appl. No. 14/755,766, dated Aug. 18, 2017.
U.S. Office Action for U.S. Appl. No. 14/755,766, dated Aug. 6, 2018.
U.S. Office Action for U.S. Appl. No. 14/755,766, dated Dec. 9, 2016.
U.S. Office Action for U.S. Appl. No. 14/755,766, dated Jan. 13, 2020.
U.S. Office Action for U.S. Appl. No. 14/755,766, dated Jul. 10, 2019.
U.S. Office Action for U.S. Appl. No. 14/755,766, dated Mar. 21, 2018.
U S. Office Action for U.S. Appl. No. 14/755,766, dated Nov. 14. 2018.
U.S. Office Action for U.S. Appl. No. 14/755,766, dated Oct. 25, 2019.
U.S. Office Action for U.S. Appl. No. 14/755,766, dated Sep. 21, 2016.
Chinese Office Action and Search Report, dated Jul. 13, 2020, for Chinese Application No. 201710446982.0, with an English translation.

\* cited by examiner

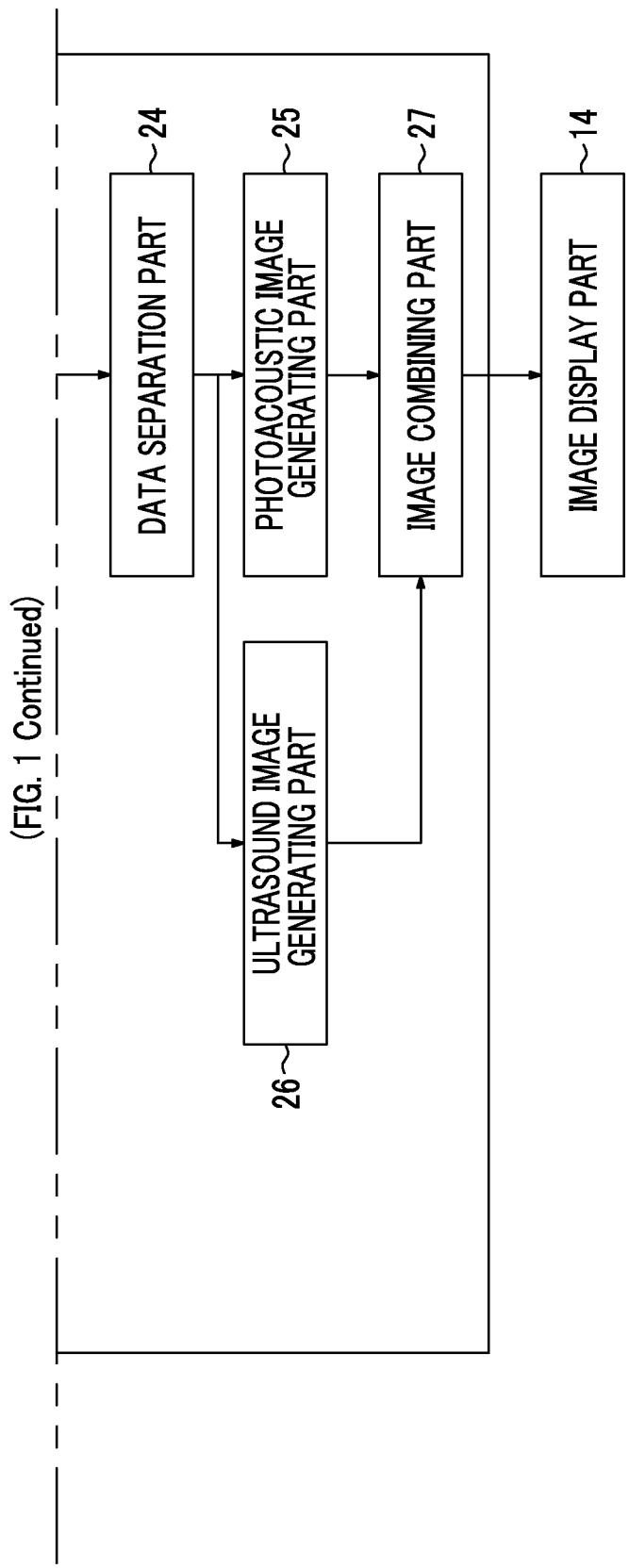
(FIG. 1 Continued)

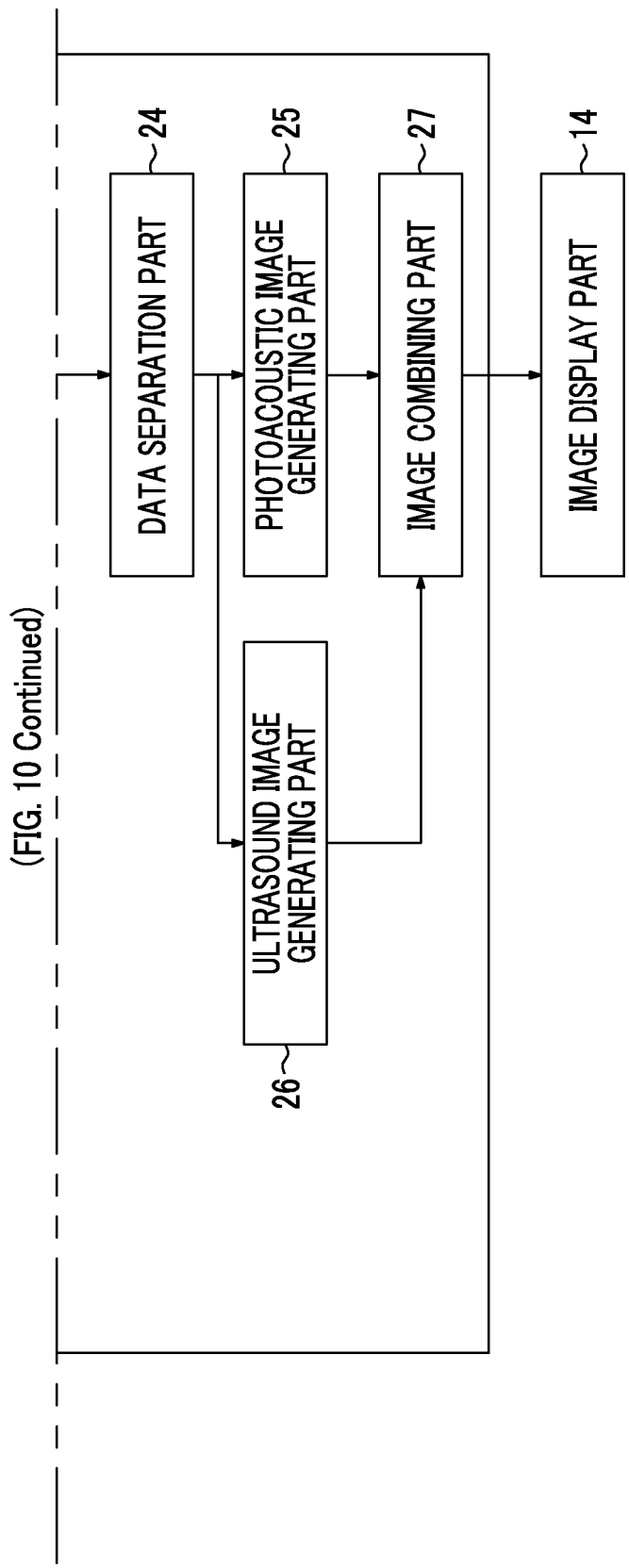

PHOTOACOUSTIC IMAGE GENERATING DEVICE AND INSERTION OBJECT

CROSS-REFERENCE TO RELATED APPLICATIONS

This application is a Divisional of U.S. application Ser. No. 14/755,766 filed on Jun. 30, 2015, which is a Continuation of PCT International Application No. PCT/JP2013/082617 filed on Dec. 4, 2013, which claims priority under 35 U.S.C. § 119(a) to Japanese Patent Application No. 2013-001519 filed on Jan. 9, 2013, Japanese Patent Application No. 2013-149497 filed on Jul. 18, 2013 and Japanese Patent Application No. 2013-247739 filed on Nov. 29, 2013. Each of the above applications is hereby expressly incorporated by reference, in its entirety, into the present application.

BACKGROUND OF THE INVENTION

1. Field of the Invention

The present invention relates to a photoacoustic image generating device that generates a photoacoustic image on the basis of photoacoustic waves generated due to the irradiation of light. Further, the present invention relates to an insertion object which is used in the photoacoustic image generating device and of which at least a tip portion is inserted into a subject.

2. Description of the Related Art

An ultrasonic inspection method is known as one kind of image inspecting method that can inspect the internal state of a living body in a non-invasive manner. An ultrasonic probe, which can transmit and receive ultrasonic waves, is used for ultrasonic inspection. When ultrasonic waves are transmitted to a subject (living body) from the ultrasonic probe, the ultrasonic waves travel in the living body and are reflected by a tissue interface. When a distance is calculated on the basis of a time until the reflected ultrasonic waves return to the ultrasonic probe after the reflected ultrasonic waves are received by the ultrasonic probe, an image of the inner state of the living body can be made.

Further, photoacoustic imaging, which makes an image of the inside of a living body by using a photoacoustic effect, is known. In general, the inside of the living body is irradiated with pulsed laser light, such as laser pulses, in photoacoustic imaging. In the living body, biological tissue absorbs the energy of the pulsed laser light and ultrasonic waves (photoacoustic waves) are generated due to adiabatic expansion caused by the energy. Since the photoacoustic waves are detected by an ultrasonic probe or the like and a photoacoustic image is formed on the basis of detection signals, the inside of the living body can be made visible on the basis of the photoacoustic waves.

Here, a combination of biological information imaging using photoacoustic waves and treatment using a puncture needle is mentioned in JP2009-31262A. In JP2009-31262A, a photoacoustic image is generated and is observed to find an affected part, such as a tumor, a portion that is suspected as an affected part, and the like. In order to more closely inspect such a portion or in order to perform injection or the like on an affected part, cells are taken or injection is performed on an affected part by using an injection needle, or a puncture needle such as a cytodiagnosis needle. In JP2009-31262A, it is possible to insert a needle to an affected part while observing the affected part, by using a photoacoustic image.

SUMMARY OF THE INVENTION

In general, it is important to ascertain the position of the tip portion of a puncture needle when inserting the puncture needle. However, the irradiation of a subject with light is generally performed from the surface of the subject. For this reason, particularly, when the tip of the puncture needle is inserted to a deep position (for example, a position at a depth from the surface of the subject of a distance of 3 cm), light applied on the surface of the subject does not sufficiently reach the puncture needle inserted to the deep position. Accordingly, it is difficult to confirm the position of the tip of the puncture needle in the photoacoustic image. Further, acoustic wave detection characteristics of the probe depend on an angle. Accordingly, as an angle of a puncture needle to be inserted exceeds 50° and approaches a right angle, photoacoustic waves are more obliquely incident on an acoustic wave detection surface of the probe. For this reason, there is also a problem in that it is difficult to detect photoacoustic waves generated from the puncture needle. In other words, there is also a problem in that it is more difficult to confirm the position of the puncture needle in the photoacoustic image as a insertion angle approaches a right angle. These problems are not limited to the puncture needle, and may be generated when the position of an insertion object to be inserted into a subject is to be confirmed using a photoacoustic image.

The invention has been made in consideration of the above-mentioned problems, and an object of the invention is to provide a photoacoustic image generating device that can confirm the position of an insertion object in a photoacoustic image even when the insertion object is inserted to a deep position from the surface of a subject or even when the insertion object is inserted into the subject at an angle close to a right angle.

In order to achieve the object, the invention provides a photoacoustic image generating device including: a first light source; an insertion object of which at least a part is inserted into a subject and which has a light guide member guiding light emitted from the first light source, a light emitting portion emitting the light guided by the light guide member, and a photoacoustic wave generating portion generating first photoacoustic waves caused by the light emitted from the light emitting portion; an acoustic wave detecting part for detecting the first photoacoustic waves that are generated from the insertion object after at least a part of the insertion object is inserted into the subject; and a photoacoustic image generating part for generating a first photoacoustic image on the basis of the first photoacoustic waves.

The insertion object may have, for example, an opening and have an inner cavity therein. The light emitting portion may be provided in the vicinity of the opening.

The photoacoustic wave generating portion of the insertion object may include a light absorbent member that absorbs the light emitted from the light emitting portion and generates photoacoustic waves. The light absorbent member may contain, for example, an epoxy resin, a fluorine resin, silicone rubber, or a polyurethane resin, into which a black pigment is mixed. Alternatively, the light absorbent member may include a film that is made of metal or a metal oxide having light absorbency with respect to the light emitted from the first light source.

The light absorbent member may cover at least a part of a light emitting surface of the light emitting portion.

The insertion object may further have a hollow tube that fixes the light guide member to an inner wall of the inner cavity along the inner cavity.

The light absorbent member may be provided on the inner wall of the inner cavity and also functions as a fixing member that fixes a tip portion of the light guide member to the inner wall.

The insertion object may be a needle that is inserted into a subject.

The needle may be a biopsy needle that is inserted into an inspection object of a living body and is capable of taking tissue of a biopsy region of the inspection object.

It is preferable that the insertion object is a needle that is inserted into a subject, and the needle further has a hollow tube that houses the light guide member therein, has the light absorbent member at a tip of the hollow tube, and has a void between the light emitting portion and the light absorbent member. The hollow tube consists of, for example, a fluorine resin, a polyimide resin, or metal such as stainless steel.

The hollow tube, the light guide member, and the light absorbent member may form an inner needle that seals at least a part of an inner cavity of a needle body.

Instead of the above, when the insertion object is a needle that is inserted into a subject, the light guide member may form an inner needle that seals at least a part of an inner cavity of the needle and at least a part of the light guide member including the light emitting portion may have a film having light absorbency.

Alternatively, when the insertion object is a puncture needle that is inserted into a subject, the needle may further have an inner needle that seals at least a part of an inner cavity of the needle, the light guide member may be embedded in the inner needle, and the inner needle may also function as the light absorbent member having light absorbency.

The insertion object may be a needle that is inserted into a subject, the needle may further have an inner needle that seals at least a part of an inner cavity, the inner needle may include a hollow tube and a transparent resin that closes at least a tip portion of the hollow tube, the light guide member may be embedded in the hollow tube by the transparent resin, and the inner needle may have the light absorbent member at a tip of the hollow tube. For example, a photo-curable resin, a thermosetting resin, or a room temperature-curable resin can be used as the transparent resin.

In the above description, the inner needle may be produced by: injecting a transparent resin, which is not yet cured, into the hollow tube; inserting the light guide member into the hollow tube so that the light emitting end of the light guide member forming the light emitting portion is disposed in the vicinity of the tip portion of the hollow tube; curing the transparent resin while the light guide member is inserted into the hollow tube; cutting the tips of the hollow tube and the transparent resin into a shape suitable for the tip of the needle; applying a resin, which has light absorbency and forms the light absorbent member, so that the resin covers at least a part of the cut surfaces of the hollow tube and the transparent resin; and curing the resin that has light absorbency.

Alternatively, the insertion object may be a needle that is inserted into a subject; the needle may further have an inner needle that seals at least a part of an inner cavity; the inner needle may include a hollow tube and a transparent resin that closes at least a tip portion of the hollow tube, and may have the light absorbent member at a light emitting end of the light guide member forming the light emitting portion; and the light guide member may be embedded in the hollow tube by the transparent resin.

In the above description, the inner needle may be produced by: attaching a light-absorbent resin, which forms the light absorbent member, to the light emitting portion so that the light-absorbent resin covers at least a part of the light emitting portion; curing the light-absorbent resin; injecting a transparent resin, which is not yet cured, into the hollow tube; inserting the light guide member into the hollow tube so that the light absorbent member is disposed in the vicinity of the tip portion of the hollow tube; curing the transparent resin while the light guide member is inserted into the hollow tube; and cutting the tips of the hollow tube and the transparent resin into a shape suitable for the tip of the needle.

The hollow tube consists of, for example, polyimide, a fluorine resin, or metal.

The needle may further comprise an optical connector that detachably connects the light guide member to an optical fiber guiding the light emitted from the first light source.

In the invention, the light emitting portion may be capable of emitting at least a part of the light, which is guided by the light guide member, toward the inner wall of the inner cavity.

The light guide member may be an optical fiber, and an end face of the optical fiber, to which light travels when seen from the first light source, may form the light emitting portion.

The insertion object may be a catheter that is inserted into a blood vessel, and may be a guide wire for a catheter that is inserted into a blood vessel.

Further, the insertion object may be a radiofrequency cauterization needle that houses an electrode used for radiofrequency cauterization therein. In this case, the electrode may be capable of protruding from an inner cavity of the radiofrequency cauterization needle, and the radiofrequency cauterization needle may further have a light guide member for the electrode that guides the light emitted from the first light source, a light emitting portion for the electrode that is provided at a tip portion of the electrode and emits the light guided by the light guide member for the electrode, and a light absorbent member for the electrode that generates photoacoustic waves due to the light emitted from the light emitting portion for the electrode.

The insertion object may be an optical fiber for laser treatment and may have a light absorbent member that absorbs light emitted from the optical fiber and generates photoacoustic waves, and the optical fiber may also function as the light guide member.

An angle of the end face of the optical fiber forming the light emitting portion may be equal to or larger than 45° and smaller than 90° when an angle in a direction parallel to an extending direction of the optical fiber is 0° and an angle in a direction perpendicular to the extending direction of the optical fiber is 90°.

The optical fiber may be connected to the first light source through an optical joint that includes a mechanism pressing and fixing the optical fiber.

In the invention, the first light source may be a semiconductor laser light source. Further, the first light source may be an optical amplification type laser light source that uses a semiconductor laser light source as a seed light source.

The acoustic wave detecting part may be further capable of detecting reflected acoustic waves of acoustic waves transmitted to the subject, and the photoacoustic image generating device may further include a reflected acoustic wave-image generating part for generating a reflected acoustic wave-image on the basis of the reflected acoustic waves.

The photoacoustic image generating device of the invention may further include an image combining part for combining the first photoacoustic image with the reflected acoustic wave-image.

The photoacoustic image generating device may further include a second light source, the acoustic wave detecting part may be further capable of detecting second photoacoustic waves that are generated in a subject due to light emitted from the second light source after the light emitted from the second light source is emitted to the subject, and the photoacoustic image generating part may be further capable of generating a second photoacoustic image on the basis of the second photoacoustic waves.

The second light source may also function as the first light source, and a part of the light emitted from the second light source may be branched toward the subject and a part of the light emitted from the second light source may be branched toward the insertion object.

The invention further provides an insertion object of which at least a tip portion is inserted into a subject and which is used for the photoacoustic image generating device. The insertion object has a light guide member that guides light emitted from a light source, a light emitting portion that emits the light guided by the light guide member, and a photoacoustic wave generating portion that generates photoacoustic waves caused by the light emitted from the light emitting portion.

The insertion object may be a needle that has an inner cavity therein and is inserted into the subject, and may further have an inner needle that seals at least a part of the inner cavity of the needle. In this case, the inner needle may include a hollow tube and a transparent resin that closes at least a tip portion of the hollow tube, and the light guide member may be embedded in the hollow tube by the transparent resin.

In the photoacoustic image generating device of the invention, it is possible to confirm the position of an insertion object in a photoacoustic image even when an insertion object is inserted to a deep position from the surface of a subject or even when the insertion object is inserted into the subject at an angle close to a right angle.

FIG. is a block diagram illustrating another configuration example of the laser unit.

Figures 5A, 5B, 5C:
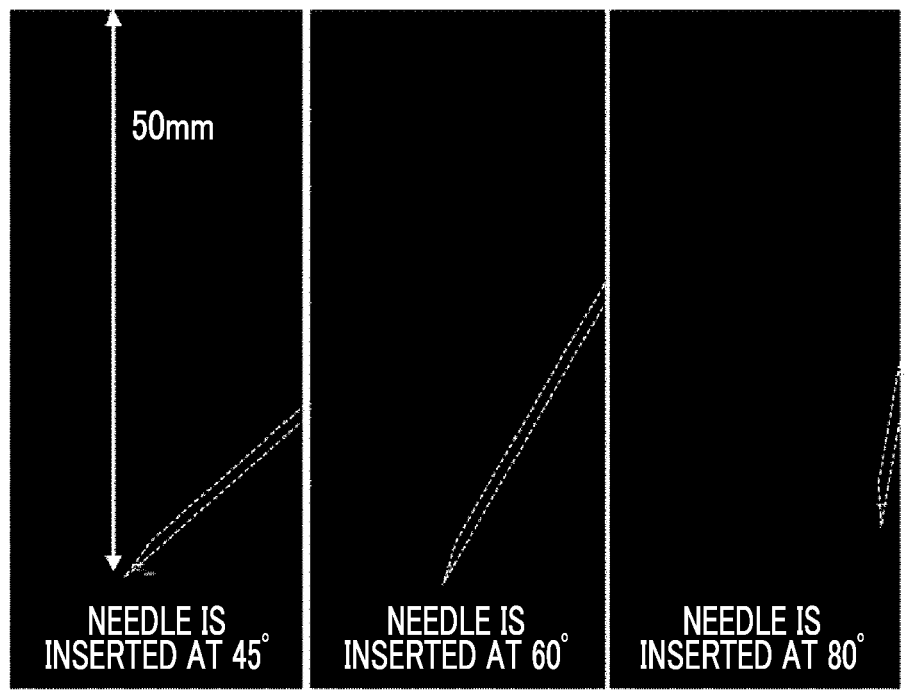

FIGS. 5A to 5C are views illustrating photoacoustic images.

Figure 6:
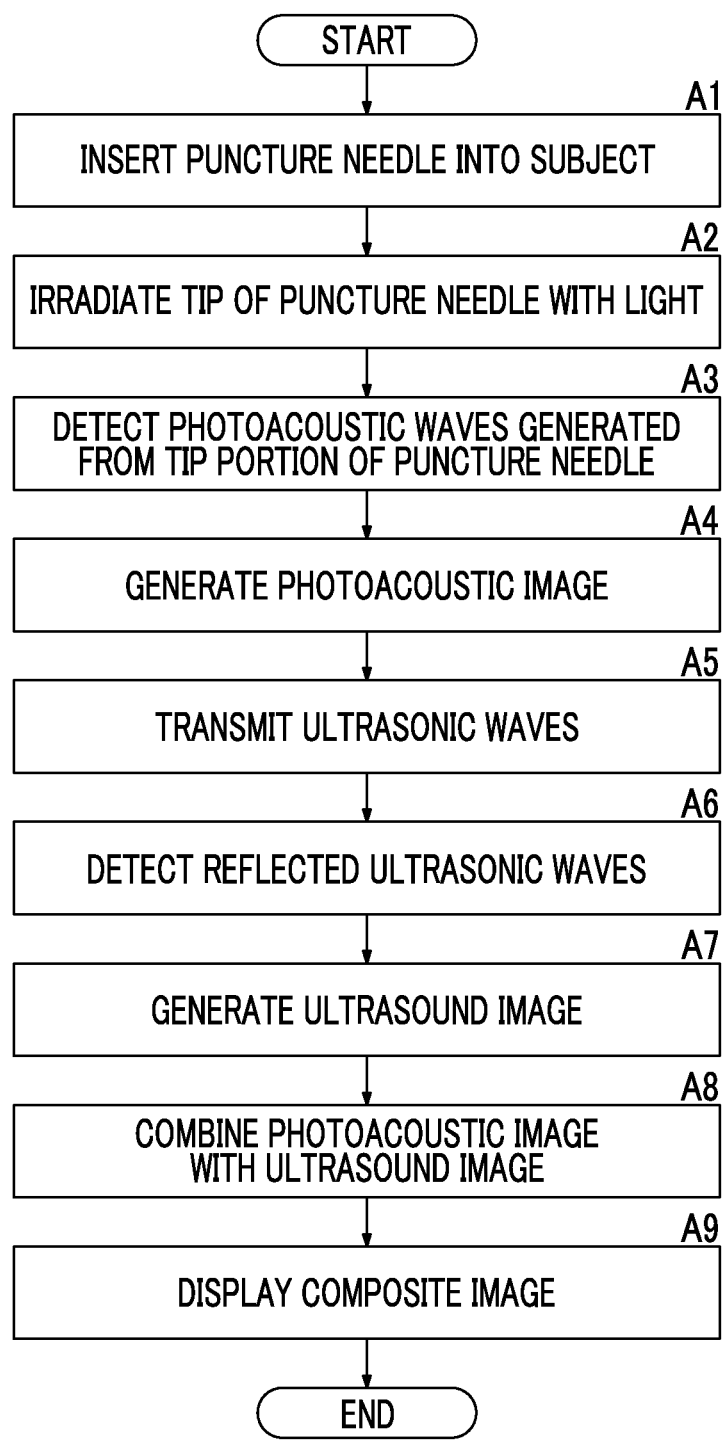

FIG. 6 is a flowchart illustrating an operation procedure of the photoacoustic image generating device according to the first embodiment.

Figure 7:
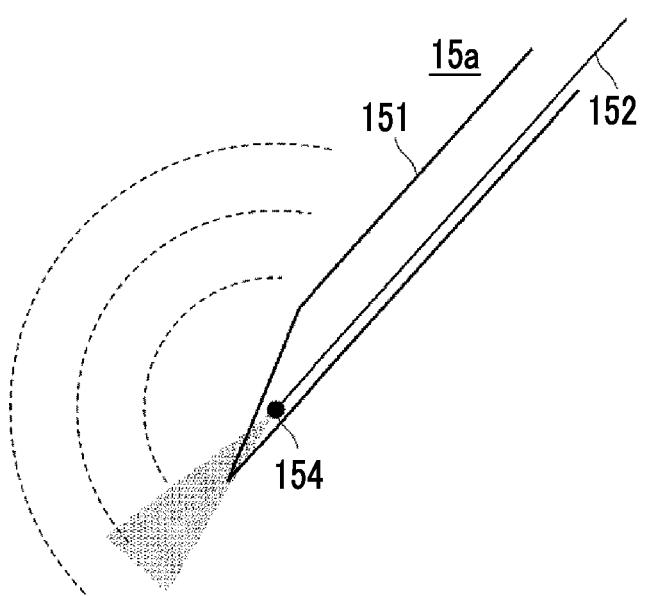

FIG. 7 is a sectional view of a puncture needle that is used in a photoacoustic image generating device according to a second embodiment of the invention.

Figure 8:
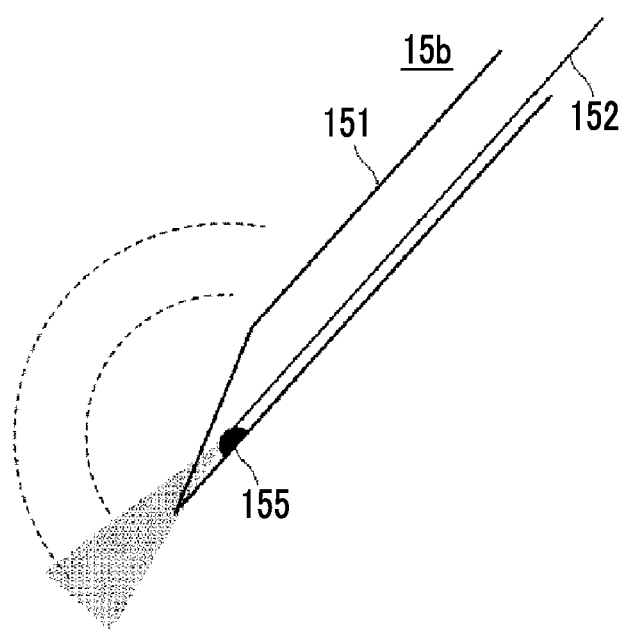

FIG. 8 is a sectional view of a puncture needle that is used in a photoacoustic image generating device according to a third embodiment of the invention.

Figure 9:
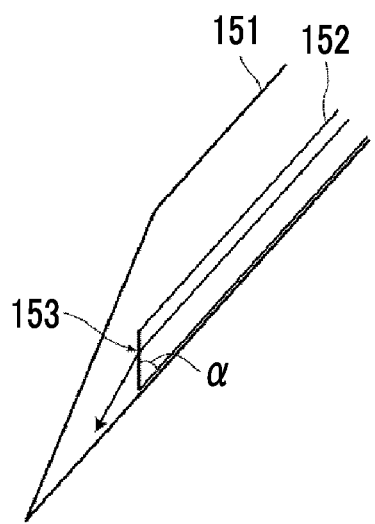

FIG. 9 is a sectional view of a puncture needle that is used in a photoacoustic image generating device according to a fourth embodiment of the invention.

Figure 10:
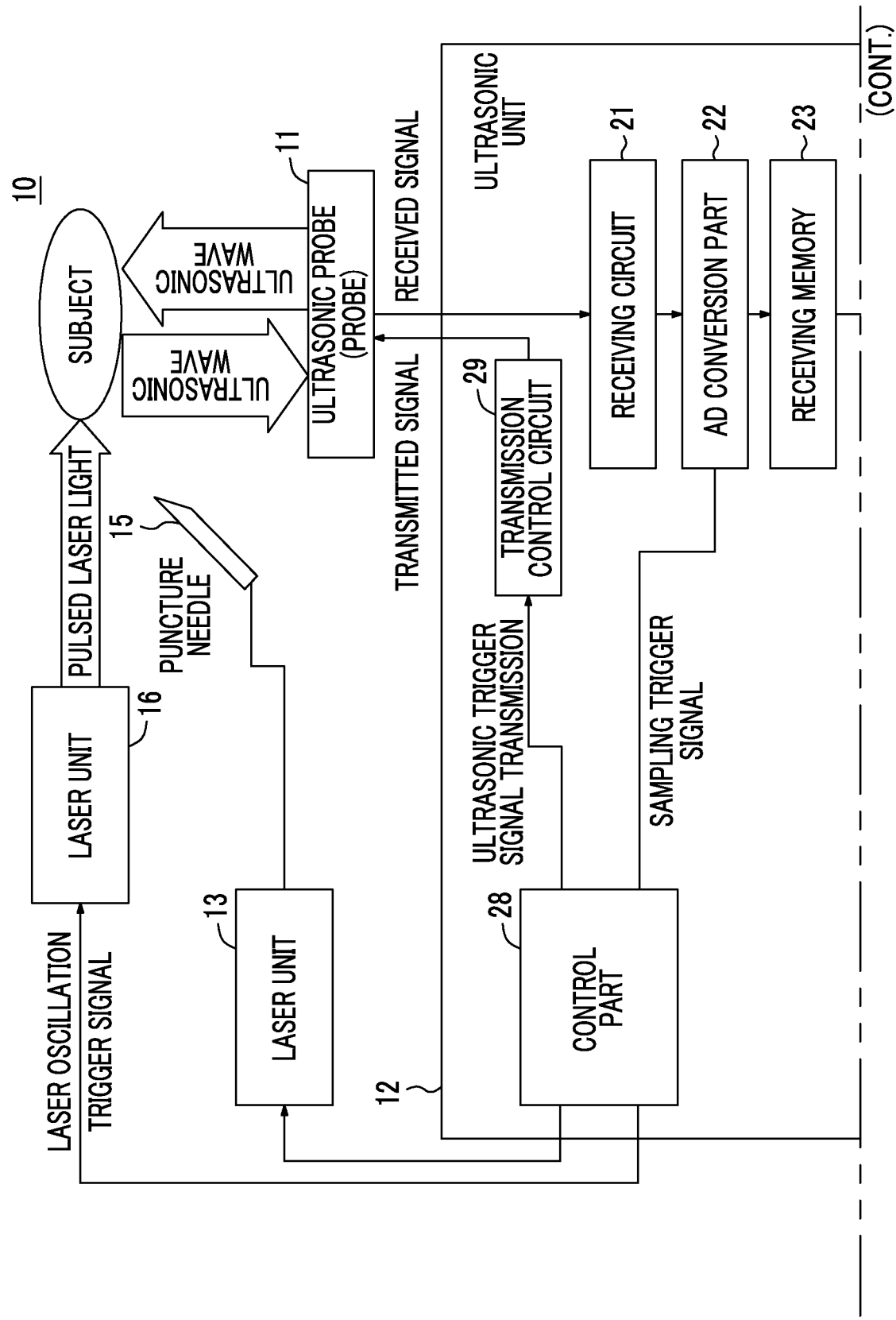

FIG. 10 is a block diagram of a photoacoustic image generating device according to a fifth embodiment of the invention.

Figure 11:
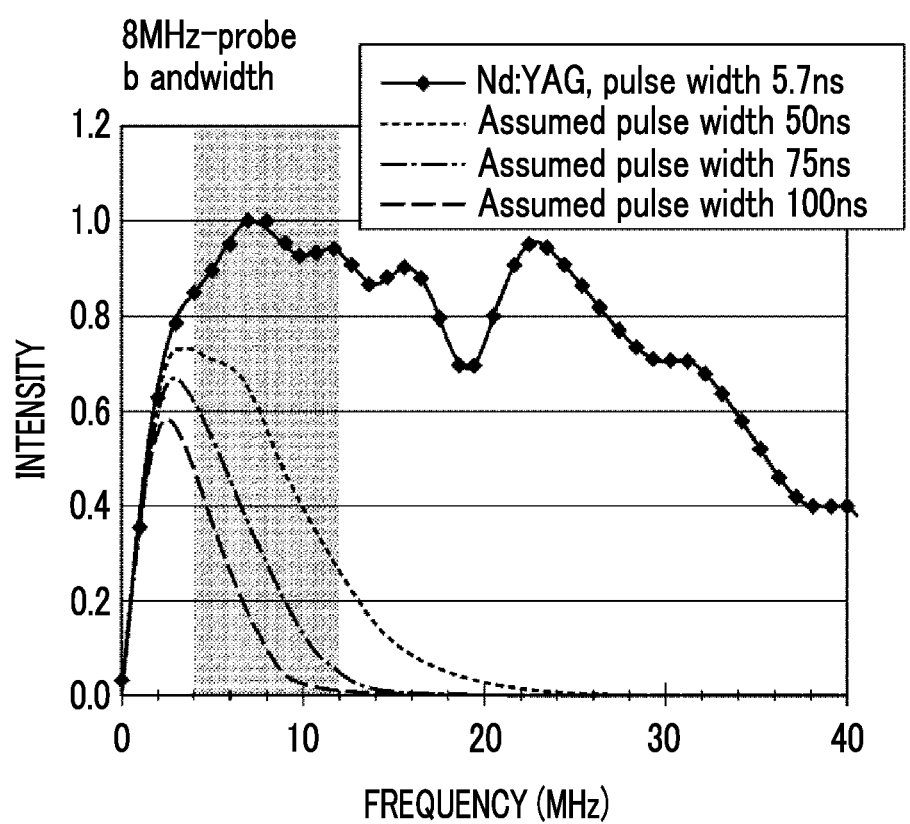

FIG. 11 is a graph illustrating the frequency characteristics of photoacoustic waves.

Figure 12:
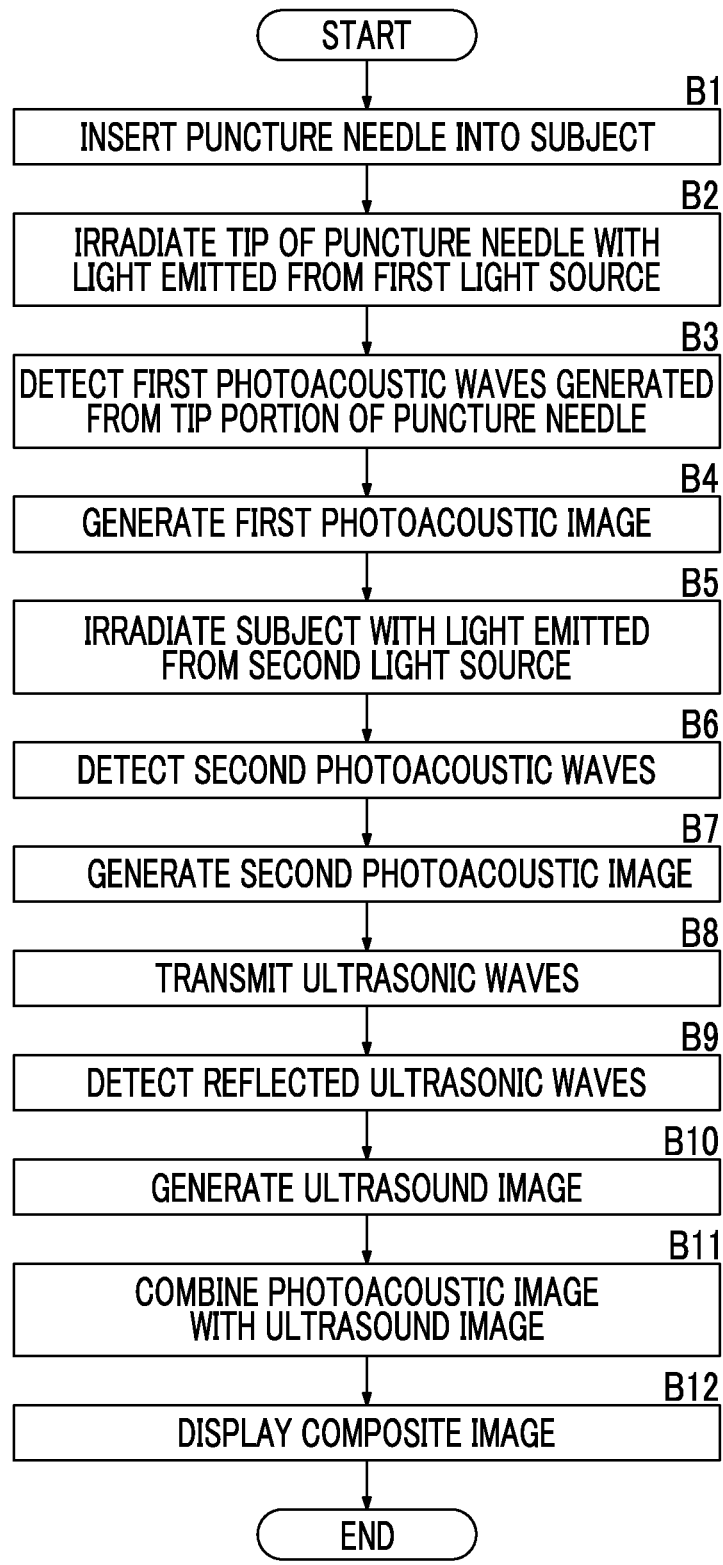

FIG. 12 is a flowchart illustrating an operation procedure of the photoacoustic image generating device according to the fifth embodiment.

Figure 13:
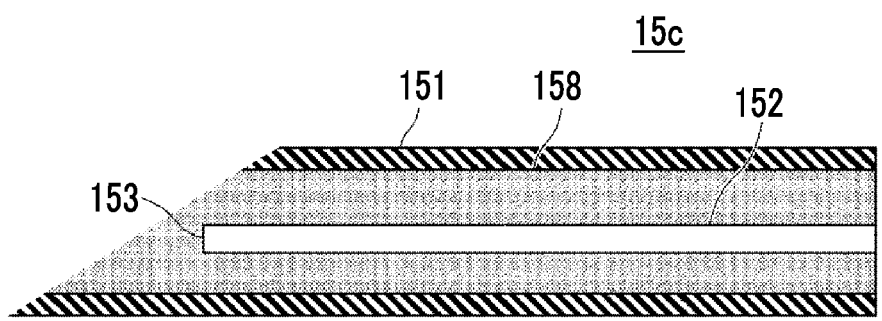

FIG. 13 is a sectional view of a puncture needle that is used in a sixth embodiment of the invention.

Figure 14A:
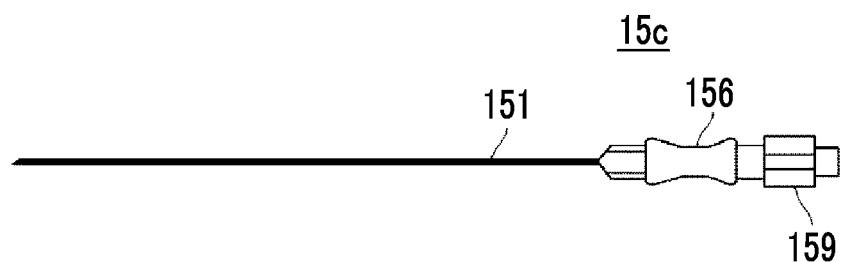
Figure 14B:
Figure 14C:

FIG. 14A is a view illustrating the appearance of the puncture needle according to the sixth embodiment, FIG. 14B is a view illustrating the appearance of a puncture needle body, and FIG. 14C is a view illustrating the appearance of an inner needle.

Figure 15:
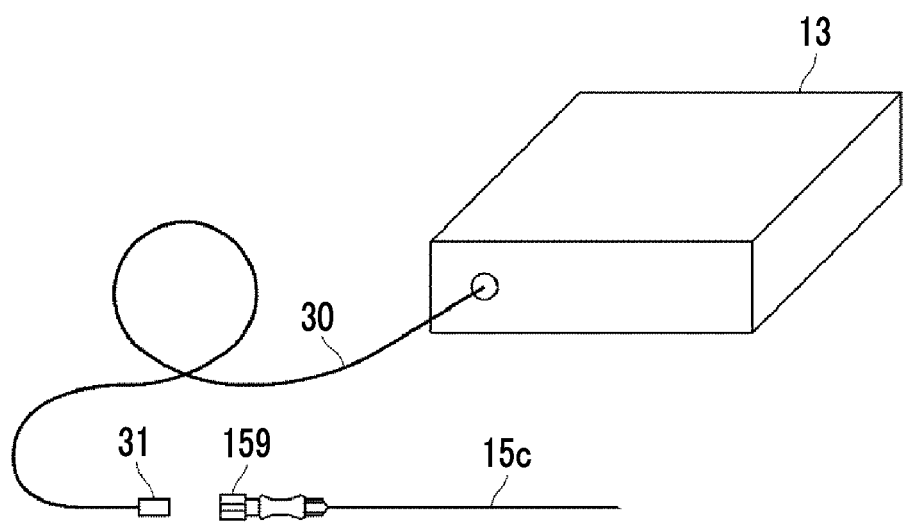

FIG. 15 is a view illustrating the connection between the laser unit and the puncture needle.

Figure 16:

FIG. 16 is a view illustrating the appearance of an inner needle that is used in a seventh embodiment of the invention.

Figure 17:
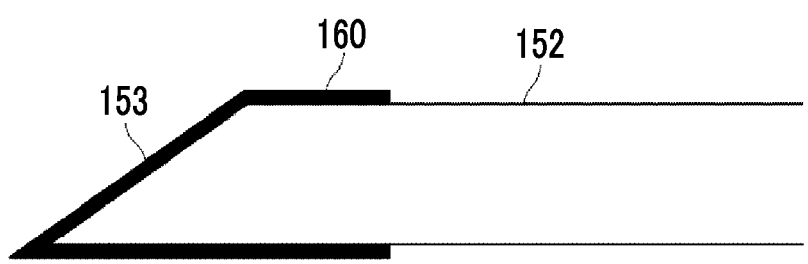

FIG. 17 is a sectional view of a tip portion of the inner needle.

Figure 18:
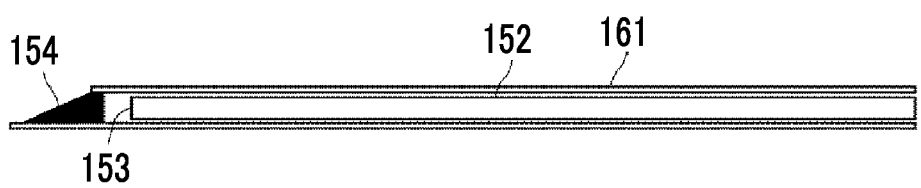

FIG. 18 is a sectional view of an inner needle that is used in an eighth embodiment of the invention.

Figure 19:
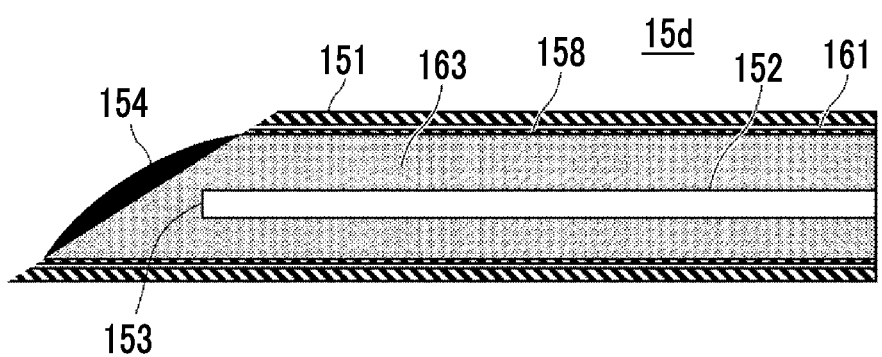

FIG. 19 is a sectional view of a puncture needle that is used in a ninth embodiment of the invention.

Figure 20:
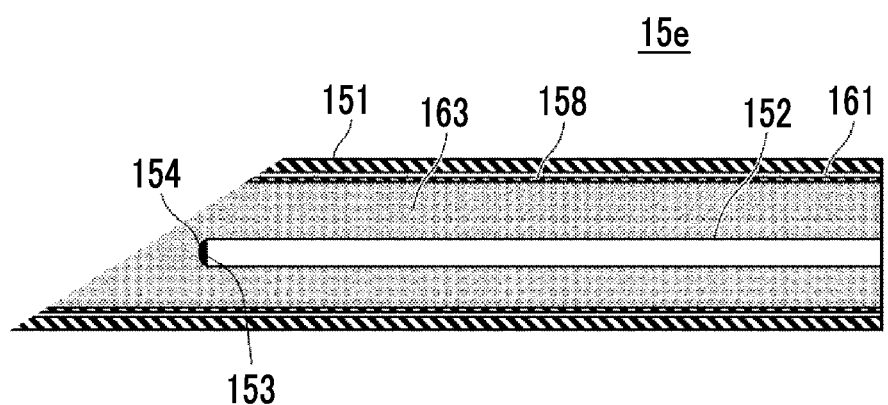

FIG. 20 is a sectional view of a puncture needle that is used in a tenth embodiment of the invention.

Figure 21:
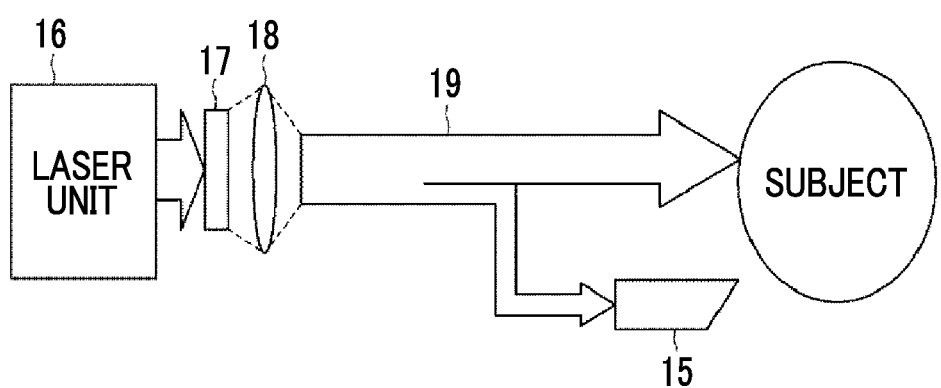

FIG. 21 is a block diagram illustrating a portion of a light source of a photoacoustic image generating device according to a modification of the fifth embodiment.

Figure 22A:
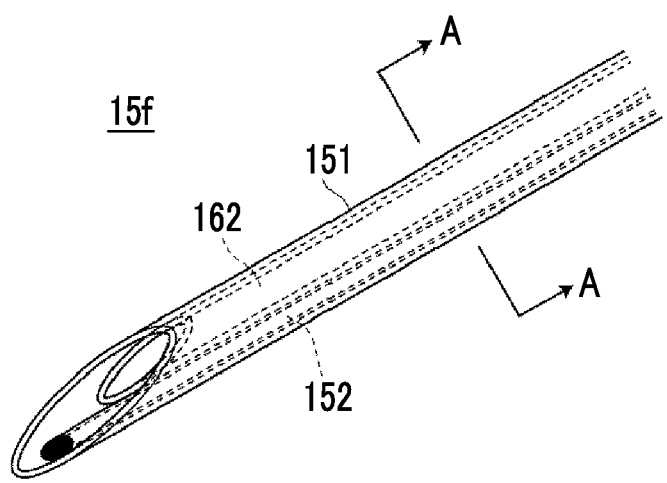
Figure 22B:
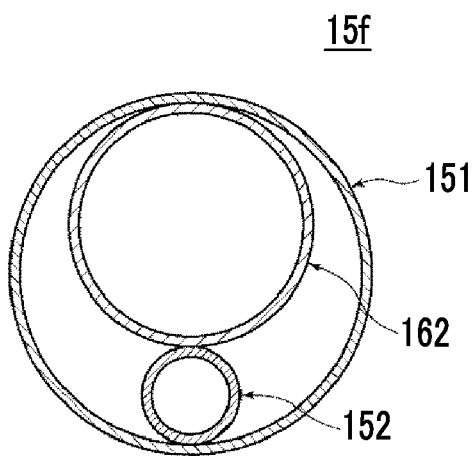

FIG. 22A is a perspective view of a puncture needle and FIG. 22B is a sectional view taken along line A-A of FIG. 22A.

Figure 23:
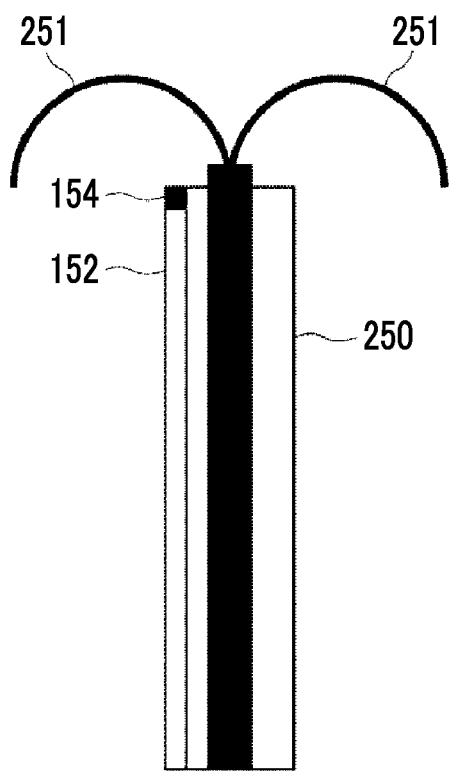

FIG. 23 is a sectional view of an example of a radiofrequency cauterization needle.

Figure 24:
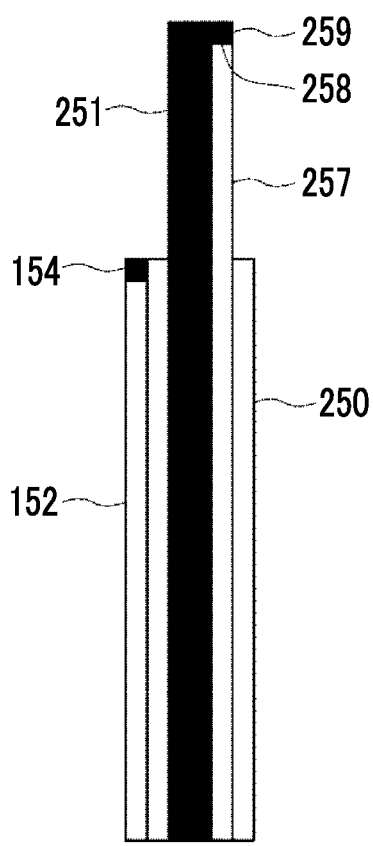

FIG. 24 is a sectional view of another example of the radiofrequency cauterization needle.

Figure 25:
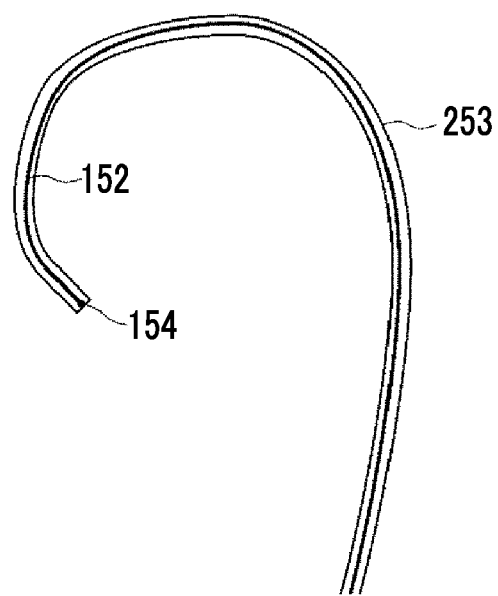

FIG. 25 is a sectional view of a catheter.

Figure 26:
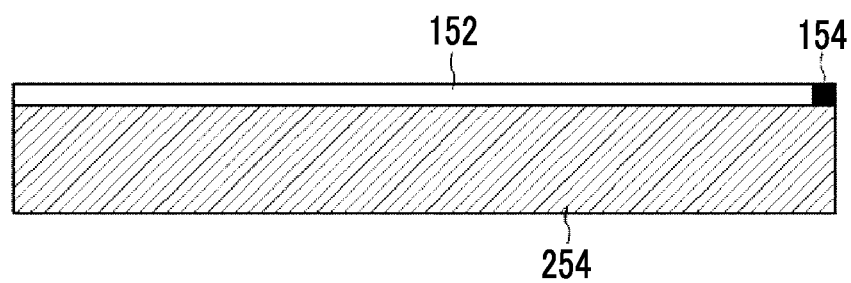

FIG. 26 is a sectional view of a guide wire.

Figure 27:
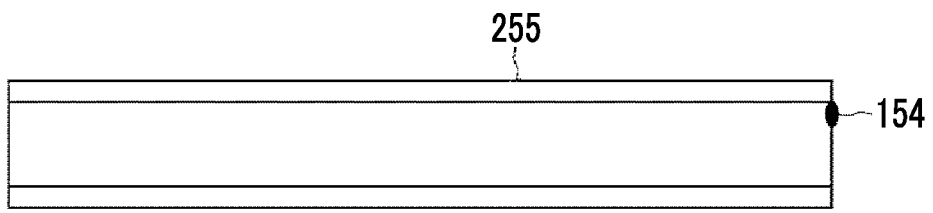

FIG. 27 is a sectional view of an example of an optical fiber for a laser treatment.

Figure 28:
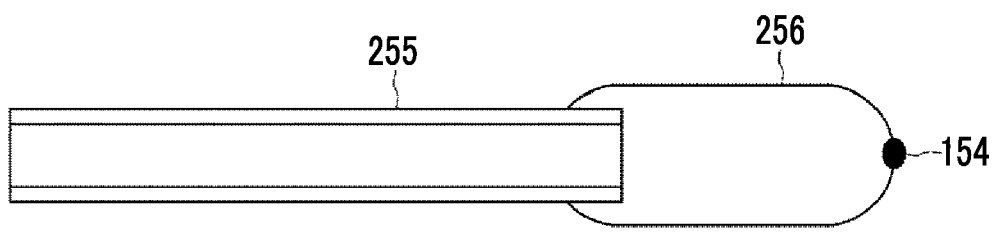

FIG. 28 is a sectional view of another example of the optical fiber for a laser treatment.

Figure 29:
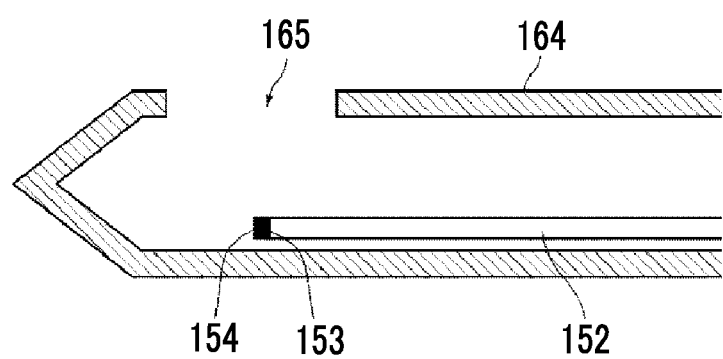

FIG. 29 is a sectional view of a tip portion of a biopsy needle.

Figure 30:
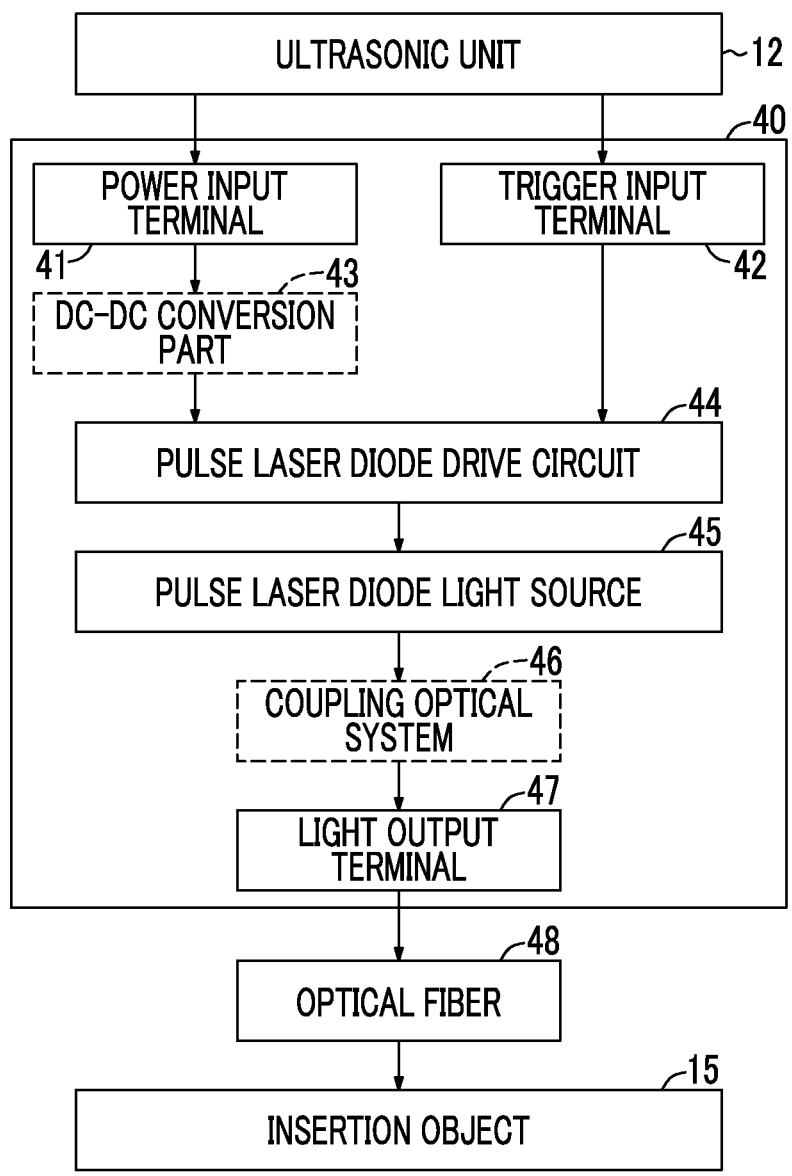

FIG. 30 is a block diagram illustrating still another configuration example of the laser unit.

Figure 31:
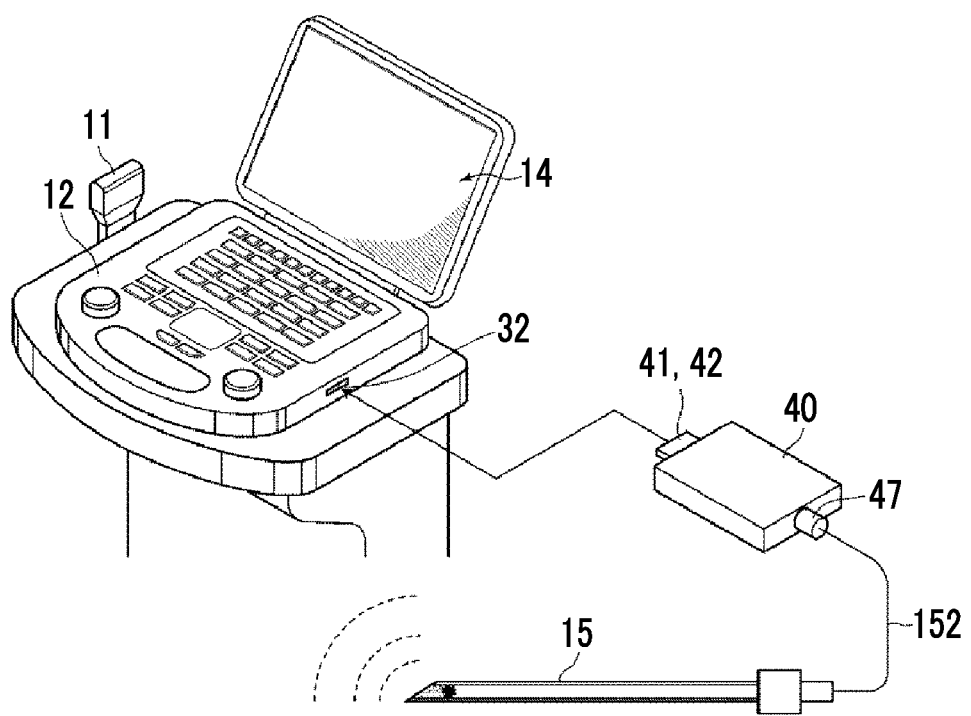

FIG. 31 is a view illustrating the appearance of a photoacoustic image generating device including the laser unit.

DESCRIPTION OF THE PREFERRED EMBODIMENTS

Figure 1:
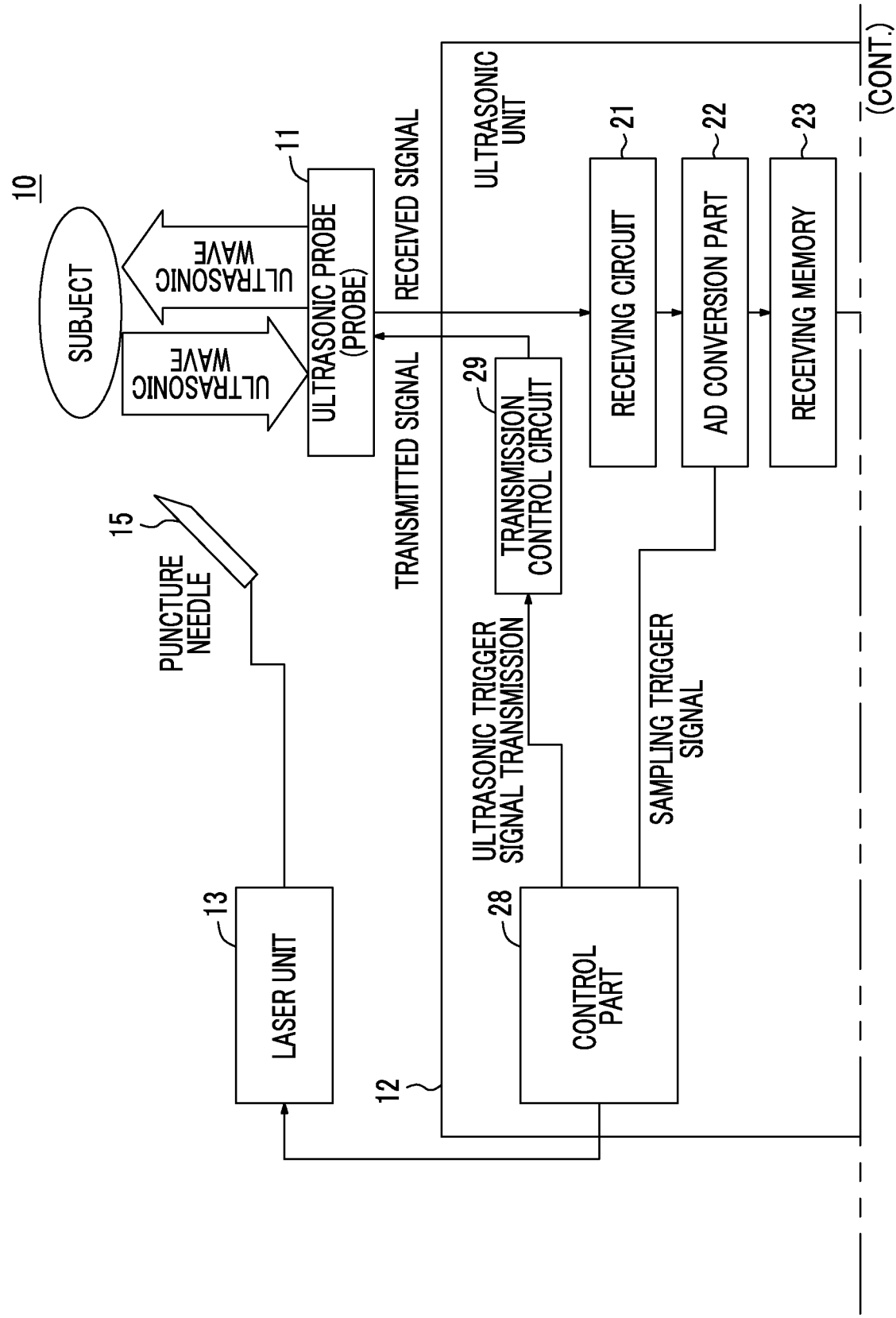
FIG. 1 is a block diagram of a photoacoustic image generating device according to a first embodiment of the invention.

Embodiments of the invention will be described in detail below with reference to the drawings. FIG. 1 illustrates a photoacoustic image generating device according to a first embodiment of the invention. The photoacoustic image generating device (photoacoustic image diagnostic device) 10 includes a probe (ultrasonic probe) 11, an ultrasonic unit 12, and a laser unit 13. Meanwhile, ultrasonic waves are used as acoustic waves in the embodiment of the invention, but the acoustic waves are not limited to the ultrasonic waves. As long as an appropriate frequency is selected according to a subject, measurement conditions, or the like, an acoustic wave having an audio frequency may be used.

The laser unit 13 is a first light source. The laser unit 13 is formed of a solid-state laser light source using, for example, YAG (yttrium aluminum garnet), alexandrite, or the like. In this embodiment, a puncture needle, which is inserted into a subject, is considered as an insertion object of which at least a tip portion is inserted into a subject. The puncture needle 15 includes an opening formed at the tip thereof and includes an inner cavity therein. Laser light emitted from the laser unit 13 is guided to the puncture needle 15 by light guide means such as an optical fiber.

Figure 2:
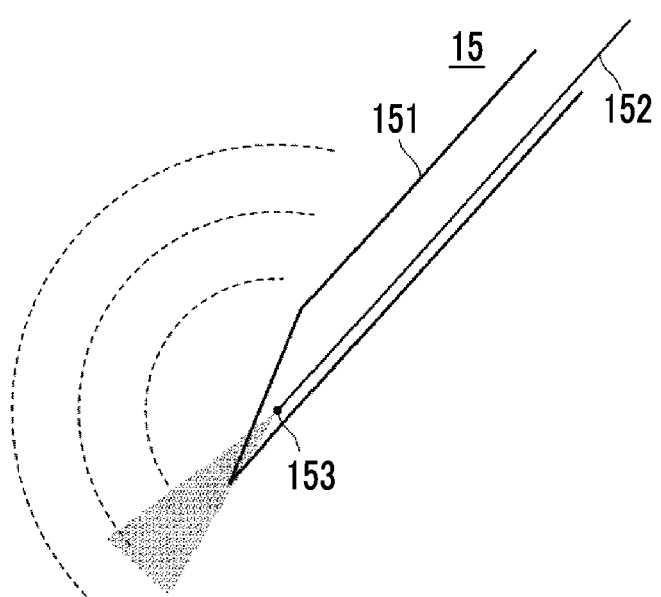
FIG. 2 is a sectional view of a puncture needle.

FIG. 2 illustrates the section of the puncture needle 15. The puncture needle 15 includes a hollow puncture needle body 151 that includes an opening formed at the tip thereof formed so as to have an acute angle and includes an inner cavity therein, a light guide member 152 that guides light emitted from the laser unit 13 to the vicinity of the opening of the puncture needle, and a light emitting portion 153 that is provided in the vicinity of the opening and emits the light guided by the light guide member. The light guide member 152 and the light emitting portion 153 are disposed in the puncture needle body 151. The light guide member 152 is formed of, for example, an optical fiber, and an end face of the optical fiber, to which light travels when seen from the laser unit 13, forms the light emitting portion 153. Laser light having an energy of, for example, 0.2 mJ is emitted from the light emitting portion 153.

The light emitting portion 153 emits at least a part of the light, which is guided by, for example, the light guide member 152, toward an inner wall of the hollow needle. The inner wall of the puncture needle 15 itself or a member provided on the inner wall forms a photoacoustic wave generating portion that absorbs light and generates photoacoustic waves. When the puncture needle 15 is inserted into the subject, the inner wall of the puncture needle 15 itself or the member provided on the inner wall, which forms the photoacoustic wave generating portion, is irradiated with at least a part, of the light emitted from the light emitting portion 153. Photoacoustic waves (first photoacoustic waves) are generated from the photoacoustic wave generating portion of the puncture needle 15 due to the irradiation of light.

Returning to FIG. 1, the probe 11 is acoustic wave detecting part and includes, for example, a plurality of ultrasonic vibrators that are arranged one-dimensionally. After the puncture needle 15 is inserted into the subject, the probe 11 detects photoacoustic waves that are generated due to the light emitted from the light emitting portion 153 (see FIG. 2). Further, the probe 11 not only detects the photoacoustic waves but also transmits acoustic waves (ultrasonic waves) to the subject and receives reflected acoustic waves reflected ultrasonic waves) of the transmitted ultrasonic waves.

The ultrasonic unit 12 includes a receiving circuit 21, AD conversion part 22, a receiving memory 23, data separation part 24, photoacoustic image generating part 25, ultrasound image generating part 26, image combining part 27, control part 28, and a transmission control circuit 29. The receiving circuit 21 receives detection signals of the photoacoustic waves that are detected by the probe 11. Furthermore, the receiving circuit 21 receives detection signals of the reflected ultrasonic waves that are detected by the probe 11. The AD conversion part 22 converts the detection signals of the photoacoustic, waves and the reflected ultrasonic waves, which are received by the receiving circuit 21, into digital signals. The AD conversion part 22 samples the detection signals of the photoacoustic waves and the reflected ultrasonic waves with a predetermined sampling period on the basis of, for example, sampling clock signals having a predetermined period. The AD conversion part 22 stores the sampled detection signals (sampling data) of the photoacoustic waves and the reflected ultrasonic waves in the receiving memory 23.

The data separation part 24 separates sampling data of the detection signals of the photoacoustic waves, which are stored in the receiving memory 23, from sampling data of the detection signals of the reflected ultrasonic waves. The data separation part 24 inputs the sampling data of the detection signals of the photoacoustic waves to the photoacoustic image generating part 25. Further, the data separation part 24 inputs the separated sampling data of the reflected ultrasonic waves to the ultrasound image generating part (reflected acoustic wave-image generating part) 26.

The photoacoustic image generating part 25 generates a photoacoustic image (first photoacoustic image) on the basis of the detection signals of the photoacoustic waves that are detected by the probe 11. The generation of the photoacoustic image includes, for example, image reconstruction, such as phase matching addition, detection, logarithmic transformation, and the like. The ultrasound image generating part 26 generates an ultrasound image (reflected acoustic wave-image) on the basis of the detection signals of the reflected ultrasonic waves that are detected by the probe 11. The generation of the ultrasound image also includes image reconstruction, such as phase matching addition, detection, logarithmic transformation, and the like.

The image combining part 27 combines the photoacoustic image with the ultrasound image. The image combining part 27 combines images for example, by superimposing the photoacoustic image and the ultrasound image. A composite image is displayed on image display part 14 such as a display. The photoacoustic image and the ultrasound image can be displayed side by side on the image display part 14 without combining images, or the photoacoustic image and the ultrasound image can also be switched.

The control part 28 controls the respective parts of the ultrasonic unit 12. The control part 28 sends a trigger signal to, for example, the laser unit 13 and causes laser light to be emitted from the laser unit 13. Further, the control part 28 sends a sampling trigger signal to the AD conversion part 22 in accordance with the irradiation of laser light, and controls the sampling start timing of the photoacoustic waves.

The control part 28 sends an ultrasonic wave transmission trigger signal, which instructs the transmission control circuit 29 to transmit ultrasonic waves, to the transmission control circuit 29 in order to acquire the ultrasound image. When receiving the ultrasonic wave transmission trigger signal, the transmission control circuit 29 causes ultrasonic waves to be transmitted from the probe 11. The control part 28 sends a sampling trigger signal to the AD conversion part 22 in accordance with an ultrasonic wave transmission timing, and starts the sampling of the reflected ultrasonic waves.

Figure 3:
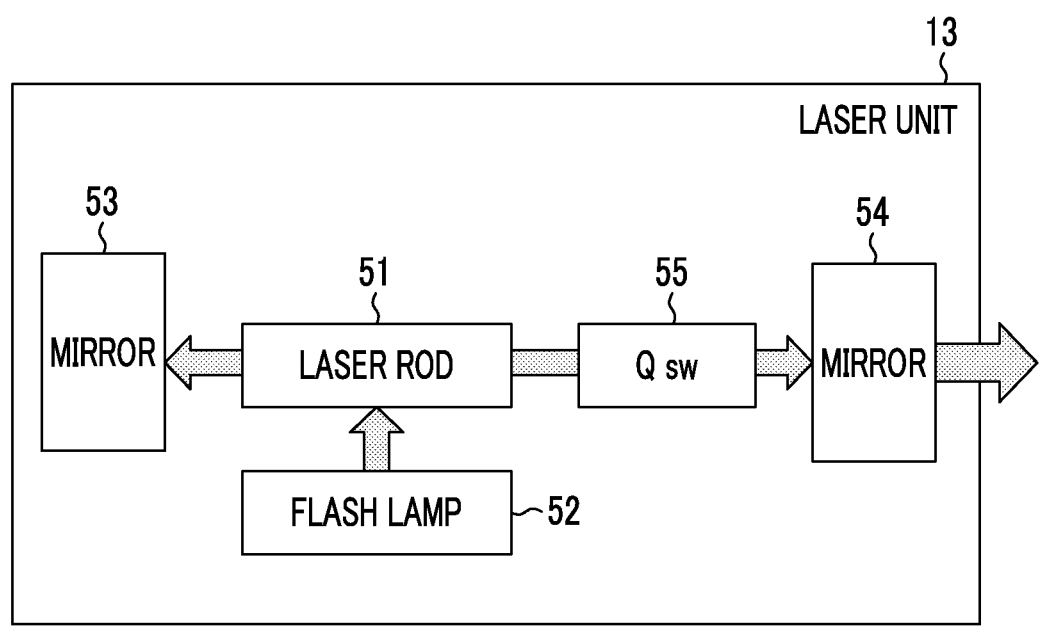
FIG. 3 is a block diagram illustrating a configuration example of a laser unit.

FIG. 3 illustrates a configuration example of the laser unit 13. The laser unit 13 includes a laser rod 51, a flash lamp 52, mirrors 53 and 54, and a Q-switch 55. The laser rod 51 is a laser medium. For example, alexandrite crystal can be used as the laser rod 51. The flash lamp 52 is an excitation light source, and irradiates the laser rod 51 with excitation light. The excitation light source is not limited to the flash lamp 52, and light sources other than the flash lamp 52 may be used as the excitation light source.

The mirrors 53 and 54 face each other with the laser rod 51 interposed therebetween, and the mirrors 53 and 54 form an optical resonator. The mirror 54 is provided on an output side. The Q-switch 55 is inserted into the optical resonator. It is possible to obtain pulsed laser light by rapidly changing an insertion loss of the optical resonator to a small loss (high Q) from a large loss (low Q) by the Q-switch 55. Pulsed laser light, which is emitted from the mirror 54 provided on the output side of the laser unit 13, is guided to the puncture needle 15 (see FIG. 1).

Figure 4:
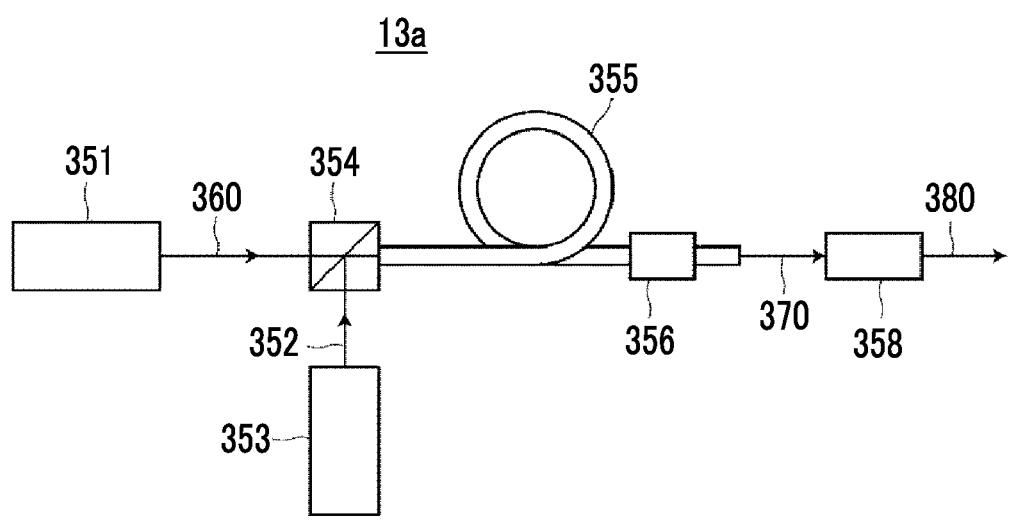

Meanwhile, the laser unit 13 does not need to be a solid-state laser light source, and may be other types of laser light source. For example, the laser unit 13 may be a laser diode light source (semiconductor laser light source). Further, the laser unit 13 may be an optical amplification type laser light source that uses a laser diode light source as a seed light source, FIG. 4 illustrates another configuration example of the laser unit. In this example, a laser unit 13a is formed of an optical amplification type laser light source. The laser unit 13a includes a semiconductor laser light source 351 that emits pulsed laser light 360 as seed light, an excitation semiconductor laser light source 353 that emits excitation laser light 352, a multiplexer 354 that multiplexes the pulsed laser light 360 and the excitation laser light 352, a fiber optical amplifier 355 that includes a core doped with, for example, Er (erbium) and is connected to the multiplexer 354, an optical isolator 356 that is connected to the fiber optical amplifier 355 and prevents oscillation, and an optical wavelength conversion element 358 that converts pulsed laser light 370 output from the optical isolator 356 into a second harmonic having a half of the wavelength of the pulsed laser light 370.

When a trigger signal is input to the semiconductor laser light source 351, which is a seed light source, from the control part 28 (see FIG. 1), the semiconductor laser light source 351 emits pulsed laser light 360 having a wavelength of, for example, 1560 nm. The pulsed laser light 360 is incident on the fiber optical amplifier 355, and is propagated through the core of the fiber optical amplifier 355. In this case, the pulsed laser light 360 is amplified by receiving energy from erbium ions that are excited by excitation laser light 352 having a wavelength of, for example, 980 nm. After being emitted from the fiber optical amplifier 355, this amplified pulsed laser light 370 is converted into pulsed laser light 380, which is a second harmonic having a wavelength of 780 nm, by the optical wavelength conversion element 358. The pulsed laser light 380, which is emitted from the laser unit 13a, is guided to the puncture needle 15 (see FIG. 1).

Meanwhile, a member (receptacle), which includes a mechanism pressing and fixing the optical fiber, can be used as an optical joint (connector) that connects the laser unit to the optical fiber of the light guide member. For example, such a receptacle is provided in the laser unit 13, and element wires of the optical fiber extending from the puncture needle 15 are inserted into the optical joint. The optical joint holds the optical fiber by a pressing force of, for example, a spring or the like. When this optical joint is used and the optical fiber is pulled so that a force equal to or larger than a certain level is applied to the receptacle, the optical fiber is separated from the receptacle. Accordingly, it is possible to prevent the optical fiber from being broken at the optical joint. Further, since a plug (connector) does not need to be provided on the optical fiber that is integrated with the puncture needle 15, it is possible to reduce the costs of the entire puncture needle. In particular, when the puncture needle 15 is disposable, the optical fiber to be discarded together with the puncture needle does not require a connector. Accordingly, an effect of reducing costs is great.

FIGS. 5A to 5C illustrate photoacoustic images. FIG. 5A illustrates a photoacoustic image when the puncture needle 15 is inserted into the subject at an angle of 45° from the surface of the subject. The puncture needle 15 is inserted into the subject to a depth of, for example, 50 mm from the surface of the subject. Light is applied to the tip portion of the puncture needle from the light emitting portion that is provided in the vicinity of the tip of the puncture needle 15, so that a photoacoustic wave is generated at the tip portion of the puncture needle 15. Accordingly, it is possible to confirm the position of the tip of the puncture needle 15 in the photoacoustic image.

FIG. 5B illustrates a photoacoustic image when the puncture needle 15 is inserted into the subject at an angle of 60° from the surface of the subject. Further, FIG. 5C illustrates a photoacoustic image when the puncture needle 15 is inserted into the subject at an angle of 80° from the surface of the subject. Even in FIGS. 5B and 5C, it is possible to confirm the position of the tip of the puncture needle 15 in the photoacoustic image as in FIG. 5A.

Here, when light is applied on the surface of a subject, a range, which is present between the surface of the subject and a portion corresponding to a depth of about 20 mm, is an imagable range. When the puncture needle 15 is inserted into the subject to a depth of 50 mm, light applied on the surface of the subject does not sufficiently reach the puncture needle 15. For this reason, it is difficult to make an image of the puncture needle 15 with light that is applied on the surface of the subject. In contrast, in this embodiment, the light guide member 152 is provided in the puncture needle 15 and light, which is guided by the light guide member 152, is applied to the tip portion of the puncture needle 15 from the light emitting portion that is provided in the vicinity of the tip portion of the puncture needle 15 inserted into the subject. Accordingly, light can be applied to the tip portion of the puncture needle 15 without being significantly attenuated. For this reason, even when the puncture needle is inserted to a deep position, it is possible to confirm the position of the puncture needle 15.

Further, when light is applied on the surface of the subject and the puncture needle 15 is inserted into the subject at an angle close to a right angle, the photoacoustic wave generated from the puncture needle 15 is obliquely incident on an acoustic wave detection surface of the probe 11. Accordingly, it is difficult to detect the photoacoustic wave that is generated from the puncture needle 15. In contrast, in this embodiment, since a photoacoustic wave is generated from the vicinity of the tip of the puncture needle 15, it is possible to confirm the position of the puncture needle 15 in the photoacoustic image even when the puncture needle 15 is inserted into the subject at an angle close to a right angle as illustrated in FIGS. 5B and 5C.

FIG. 6 illustrates an operation procedure. The puncture needle 15 is inserted into the subject by a doctor or the like (Step A1). After the puncture needle 15 is inserted into the subject, the control part 28 of the ultrasonic unit 12 sends a trigger signal to the laser unit 13. When the laser unit 13 receives the trigger signal, the laser unit 13 starts laser oscillation and emits pulsed laser light. The pulsed laser light emitted from the laser unit 13 is guided to the vicinity of the tip of the puncture needle 15 by the light guide member 152 (see FIG. 2), and is emitted from the light emitting portion 153. The tip portion of the puncture needle 15 is irradiated with at least a part of the pulsed laser light (Step A2).

The probe 11 detects photoacoustic waves that are generated in the subject due to the irradiation of laser light (Step A3). The AD conversion part 22 receives the detection signals of the photoacoustic waves through the receiving circuit 21, samples the detection signals of the photoacoustic waves, and stores the detection signals of the photoacoustic waves in the receiving memory 23. The data separation part 24 transmits the detection signals of the photoacoustic waves, which are stored in the receiving memory 23, to the photoacoustic image generating part 25. The photoacoustic image generating part 25 generates a photoacoustic image on the basis of the detection signals of the photoacoustic waves (Step A4).

The control part 28 sends an ultrasonic trigger signal to the transmission control circuit 29. The transmission control circuit 29 causes ultrasonic waves to be transmitted from the probe 11 in response to the ultrasonic trigger signal (A5). The probe 11 detects reflected ultrasonic waves after transmitting the ultrasonic waves (Step A6). Meanwhile, ultrasonic waves may be transmitted and received at positions separate from each other. For example, the ultrasonic waves may be transmitted from a position different from the position of the probe 11 and the reflected ultrasonic waves of the transmitted ultrasonic waves may be received by the probe 11.

The reflected ultrasonic waves detected by the probe 11 are input to the AD conversion part 22 through the receiving circuit 21. Here, the reflected ultrasonic waves transmitted from the probe 11 go and return and are propagated between the probe 11 and an ultrasonic wave-reflection position, but the photoacoustic waves are propagated in one direction to the probe 11 from the vicinity of the tip of the puncture needle 15 that is a position where the photoacoustic waves are generated. Accordingly, since the time required for the detection of the reflected ultrasonic waves is double the time required for the detection of the photoacoustic waves that are generated at the same depth position, the sampling clock of the AD conversion part 22 during the sampling of the reflected ultrasonic waves may be a half of that during the sampling of the photoacoustic waves. The AD conversion part 22 stores the sampling data of the reflected ultrasonic waves in the receiving memory 23.

The data separation part 24 transmits the detection signals of the reflected ultrasonic waves, which are stored in the receiving memory 23, to the ultrasound image generating part 26. The ultrasound image generating part 26 generates an ultrasound image on the basis of the detection signals of the reflected ultrasonic waves (Step A7). The image combining part 27 combines the photoacoustic image, which is generated in Step A4, with the ultrasound image that is generated in Step A7 (Step A8). A composite image formed in Step A8 is displayed on the image display part 14 (Step A9).

In this embodiment, the light guide member 152 is provided in the puncture needle 15 and the light emitting portion 153 (FIG. 2) is provided in the vicinity of the tip of the puncture needle 15. Light, which is guided in the puncture needle 15, is emitted from the light emitting portion 153 and is applied to the photoacoustic wave generating portion that is present in the vicinity of the tip of the puncture needle 15. The photoacoustic waves, which are generated at the photoacoustic wave generating portion due to the absorption of applied light, pass through the opening of the puncture needle 15, and are detected by the probe 11. It is possible to confirm the position of the puncture needle 15 in the photoacoustic image by forming the photoacoustic waves into an image. In this embodiment, light is guided to the vicinity of the tip of the puncture needle 15 by the light guide member 152 and is applied to the tip portion of the puncture needle 15 from the puncture needle 15. Accordingly, even when the puncture needle 15 is inserted to a deep position or even when the puncture needle 15 is inserted into the subject at an angle close to a right angle, it is possible to confirm the position of the puncture needle 15 in the photoacoustic image. Here, the vicinity of the tip of the puncture needle 15 means a position where photoacoustic waves capable of making an image of the position of the tip of the puncture needle 15 with an accuracy required for work for inserting the puncture needle can be generated when the light emitting portion 153 and the photoacoustic wave generating portion are disposed at the position of the tip of the puncture needle 15. For example, the vicinity of the tip of the puncture needle 15 indicates a range that is present in the range of 0 mm to 3 mm from the tip of the puncture needle 15 toward a base end thereof. The vicinity of the tip has the same meaning even in the subsequent embodiments.

Next, a second embodiment of the invention will be described. FIG. 7 illustrates the section of a puncture needle that is used in a photoacoustic image generating device according to the second embodiment of the invention. A puncture needle 15a of this embodiment is different from the puncture needle 15 illustrated in FIG. 2 and used in the first embodiment in that the puncture needle 15a further includes a light absorbent member 154. The light absorbent member 154 forms at least a part of a photoacoustic wave generating portion of the puncture needle 15a. The structure of the photoacoustic image generating device is the same as that of the first embodiment illustrated in FIG. 1.

The puncture needle 15a includes a light absorbent member 154 that is provided at a position to which light emitted from the light emitting portion of a light guide member 152 is applied. The light absorbent member 154 is provided in the vicinity of the tip of the puncture needle 15a on the inner wall of a puncture needle body 151, and absorbs light emitted from the light emitting portion and generates photoacoustic waves. The light absorbent member 154 is made of, for example, an epoxy resin, a polyurethane resin, a fluorine resin, or silicone rubber into which a black pigment is mixed, or, for example, a black paint having high light absorbency with respect to the wavelength of laser light. The light absorbent member 154 is drawn in FIG. 7 so as to be larger than the light guide member 152, but is not limited thereto. The diameter of the light absorbent member 154 may be the same as that of the light guide member 152.

Instead of the above-mentioned materials, a metal film or an oxide film having light absorbency with respect to the wavelength of laser light may be used as the light absorbent member 154. For example, a film made of an oxide, such as an iron oxide, a chromium oxide, or a manganese oxide, having high light absorbency with respect to the wavelength of laser light can be used as the light absorbent member 154. Alternatively, a film made of a metal, such as Ti or Pt, of which the light absorbency is lower than the light absorbency of an oxide but the biocompatibility is higher than the biocompatibility of an oxide, may be used as the light absorbent member 154. Further, a position at which the light absorbent member 154 is provided is not limited to the inner wall of the puncture needle body 151. For example, the metal film or the oxide film, which is the light absorbent member 154, may be formed on the light emitting portion 153 (see FIG. 2) by deposition or the like so as to have a thickness of, for example, about 100 nm, and the oxide film may cover the light emitting portion 153. In this case, at least a part of the light emitted from the light emitting portion 153 is absorbed by the metal film or the oxide film covering a light emitting surface, so that photoacoustic waves are generated from the metal film or the oxide film.

In this embodiment, the puncture needle 15a includes the light absorbent member 154. Since the light absorbent member 154 is irradiated with light emitted from the laser unit 13, it is possible to enhance the photoacoustic waves, which are generated from the tip portion of the puncture needle, in comparison with a case in which the light absorbent member 154 is not provided. For this reason, even when the energy of the light emitted from the laser unit 13 is low, it is possible to efficiently generate photoacoustic waves. Other effects are the same as those of the first embodiment.

Subsequently, a third embodiment of the invention will be described. FIG. 8 illustrates the section of a puncture needle that is used in a photoacoustic image generating device according to the third embodiment of the invention. A puncture needle 15b of this embodiment is different from the puncture needle 15a illustrated in FIG. 7 and used in the second embodiment in that a light absorbent member 155 also functions as a fixing member for fixing a light guide member 152 to the inner wall of a puncture needle. The structure of the photoacoustic image generating device is the same as that of the first embodiment illustrated in FIG. 1.

The light absorbent member 155, which is also a fixing member, is made of, for example, an epoxy resin, a polyurethane resin, a fluorine resin, silicone rubber, or the like into which a black pigment is mixed. The light absorbent member 155 covers a light emitting end of an optical fiber that is, for example, the light guide member 152 and fixes the end face of the optical fiber to the inner wall of a puncture needle body 151. Accordingly, it is possible to fix the light guide member 152, and to accurately ascertain a positional relationship between the tip of the puncture needle 15b and the tip (light emitting portion) of the light guide member 152. Other effects are the same as those of the second embodiment.

Next, a fourth embodiment of the invention will be described. FIG. 9 illustrates the section of a puncture needle that is used in a photoacoustic image generating device according to the fourth embodiment of the invention. This embodiment is different from the first embodiment in that a light emitting end face (light emitting portion 153) of an optical fiber forming the light guide member 152 is formed obliquely. The structure of the photoacoustic image generating device is the same as that of the first embodiment illustrated in FIG. 1. Meanwhile, also in this embodiment, the puncture needle may include the light absorbent member 154 (see FIG. 7) as in the second embodiment. Further, as in the third embodiment, the puncture needle may include the light absorbent member 155 (see FIG. 8) also functioning as a fixing member.

In this embodiment, an end face of the light guide member (optical fiber) 152 forming the light emitting portion 153 is inclined at an angle α without being perpendicular. In more detail, the angle of the end face of the optical fiber forming the light guide member 152 is equal to or larger than 45° and smaller than 90° when it is assumed that an angle in a direction parallel to an extending direction of the optical fiber is 0° and an angle in a direction perpendicular to the extending direction of the optical fiber is 90°. When the refractive index of the optical fiber (core) is about 1.45 and the puncture needle 15 is filled with air or water, light having travelled through the optical fiber is refracted toward the inner wall of the puncture needle 15 at the light emitting end face of the optical fiber. Accordingly, since the inner wall of the puncture needle 15 can be irradiated with more light, it is possible to allow the puncture needle 15 to efficiently generate photoacoustic waves at the tip portion of the puncture needle.

Subsequently, a fifth embodiment of the invention will be described. FIG. 10 illustrates a photoacoustic image generating device according to the fifth embodiment of the invention. The photoacoustic image generating device according to this embodiment includes a laser unit 16 (second light source) in addition to the photoacoustic image generating device 10 according to the first embodiment illustrated in FIG. 1. Meanwhile, also in this embodiment, a puncture needle may include the light absorbent member 154 (see FIG. 7) as in the second embodiment and the puncture needle may include the light absorbent member 155 (see FIG. 8) also functioning as a fixing member as in the third embodiment. Further, the light emitting end of an optical fiber may be formed obliquely as in the fourth embodiment (see FIG. 9).

The laser unit 16 emits laser light that is applied to a subject from the surface or the like of the subject. The wavelength of the laser light may be appropriately set according to a biological tissue or the like of an object to be observed. The laser unit 16 is formed of, for example, a solid-state laser light source that uses alexandrite as a laser medium. Light emitted from the laser unit 16 is guided to the probe 11 by an optical fiber or the like, and is applied to the subject from a light irradiation portion that is provided on the probe 11. Laser light may be applied from a portion other than the probe 11 instead of being applied from the probe 11. After the subject is irradiated with the light emitted from the laser unit 16, the probe 11 detects photoacoustic waves (second photoacoustic waves) that are generated due to the irradiation of light.

Since a relatively large area of the subject is irradiated with the light emitted from the laser unit 16 as the second light source, it is preferable that the laser unit 16 emits laser light having high energy. In contrast, since only a limited area of the tip of the puncture needle 15 has only to be irradiated with the light emitted from the laser unit 13 as the first light source and has high energy density, the first light source may not be a high-output laser light source. For example, when each of the laser unit 13 and the laser unit 16 is formed of a solid-state laser light source that uses a flash lamp as an excitation light source, the flash lamp of the laser unit 13 may generate light at low intensity in comparison with the laser unit 16.

The wavelength of laser light of the laser unit 13 may be different from that of the laser unit 16. For example, a laser light source having a wavelength in the range of 700 nm to 800 nm, which can efficiently make an image of a blood vessel as an object to be observed, can be used as the laser unit 16 that is the second light source. Meanwhile, a laser light source having a wavelength of 1064 nm or 532 nm can be used as the laser unit 13 that is the first light source. It is particularly preferable that the wavelength of the laser light emitted from the laser unit 13 is in a wavelength range (700 nm to 1100 nm) in which the laser light has high transmittance in biological tissue without being absorbed locally even when the light emitted from the laser unit 13 is incident on a living body. Further, different types of laser light source may be used as the laser units 13 and 16. For example, a semiconductor laser light source or an optical amplification type laser light source may be used as the laser unit 13, and a solid-state laser light source of Nd:YAG (neodymium YAG), YAG, alexandrite, or the like may be used as the laser unit 16.

Driving conditions of the laser unit 13 will be considered. Frequency components of photoacoustic waves, which are generated at the tip portion of the puncture needle 15 after light is emitted from the laser unit 13, change depending on the pulse width of pulsed laser light emitted from the laser unit 13. FIG. 11 is a graph illustrating the frequency characteristics of photoacoustic waves that are generated due to the irradiation of pulsed laser light. In the graph, a horizontal axis represents a frequency and a vertical axis represents the intensity of a signal. FIG. 11 illustrates measured values of the frequency characteristics (a) of a photoacoustic wave with respect to pulsed laser light having a pulse width of 5.7 ns. Further, FIG. 11 also illustrates calculated values of the frequency characteristics (b) of a photoacoustic wave that is assumed when a pulse width is set to 50 ns, calculated values of the frequency characteristics (c) of a photoacoustic wave that is assumed when a pulse width is set to 75 ns, and calculated values of the frequency characteristics (d) of a photoacoustic wave that is assumed when a pulse width is set to 100 ns. The vertical axis is standardized as the maximum intensity of a photoacoustic wave with respect to a pulse width of 5.7 ns. A solid-state laser light source of Nd:YAG is used as the laser unit 13.

Referring to FIG. 11, it is understood that the high-frequency components of photoacoustic waves become weak as a pulse width is reduced. Furthermore, it is understood that the intensity of the overall photoacoustic wave is also reduced. The range of frequency, which can be detected by a general medical probe, is a range of 2 MHz to 20 MHz. For example, an acoustic wave in the range of 4 MHz to 12 MHz can be detected by a probe having a center frequency of 8 MHz. In order to cause a photoacoustic wave, which is generated at the tip portion of the puncture needle 15, to be detected by using a general medical probe, it is preferable that the laser unit 13 emits pulsed laser light having a pulse width where a photoacoustic wave having sufficient intensity in the range of frequency capable of being detected by the probe is generated. When the pulse width of the pulsed laser light exceeds 100 ns, the signal of a frequency component in the range of 2 MHz to 20 MH does not have sufficient intensity. For this reason, it is preferable that the upper limit of the pulse width is set to 100 ns. Meanwhile, when a laser diode light source is used as the laser unit 13, the intensity of pulsed laser light is substantially proportional to a pulse width. Accordingly, as a pulse width is reduced, the intensity of overall laser light is reduced. It is considered that a pulse width of at least 5 ns is needed to generate photoacoustic waves, which have an intensity capable of being detected by the probe 11, at the tip portion of the puncture needle 15. In summary, it is preferable that the pulse width of the pulsed laser light emitted from the laser unit 13 is in the range of 5 ns to 100 ns.

As a result of experiments, it was possible to make the photoacoustic waves, which are generated at the tip of the puncture needle 15, visible when the energy of the pulsed laser light was equal to or larger than 0.8 µJ in one pulse. Considering averaging, averaging can be performed 1000 times. In that case, when the energy of the pulsed laser light is equal to or larger than 0.03 µJ in one pulse, the energy of the pulsed laser light reaches a level where the photoacoustic waves can be made visible. When the upper limit of the energy is higher than 50 µJ in one pulse, an energy density is equal to or greater than 160 mJ/cm$^2$ at a core fiber having a diameter of 200 µm and an energy density is equal to or higher than 40 mJ/cm$^2$ even at a core fiber having a diameter of 400 µm. Accordingly, the energy of the pulsed laser light reaches the same level as a reference value of biological safety (20 mJ/cm$^2$ to 100 mJ/cm$^2$ at a wavelength in the range of 750 m to 1064 nm). Therefore, it is not preferable that the energy is higher than 50 µJ In summary, it is preferable that energy per pulse is in the range of 0.03 µJ to 50 µJ.

Two kinds of irradiation of light are performed in this embodiment. One of the two kinds of irradiation of light is the irradiation of the tip portion of the puncture needle 15 with the light emitted from the laser unit 13, and the other thereof is the irradiation of the subject with the light emitted from the laser unit 16. In this embodiment, the second photoacoustic waves, which are generated due to the irradiation of the subject with light, are detected in addition to the first photoacoustic waves that are generated due to the irradiation of the tip portion of the puncture needle 15 with light. The photoacoustic image generating part 25 generates a second photoacoustic image based on the second photoacoustic waves in addition to a first photoacoustic image based on the first photoacoustic waves.

FIG. 12 illustrates an operation procedure of this embodiment. The puncture needle 15 is inserted into the subject by a doctor or the like (Step B1). After the puncture needle 15 is inserted, the control part 28 of the ultrasonic unit 12 sends a trigger signal to the laser unit 13 that is the first light source. When the laser unit 13 receives the trigger signal, the laser unit 13 starts laser oscillation and emits pulsed laser light. The pulsed laser light emitted from the laser unit 13 is guided to the vicinity of the tip of the puncture needle 15 by the light guide member 152 (see FIG. 2), is emitted from the light emitting portion 153, and is applied to the tip portion of the puncture needle 15 (Step B2).

The probe 11 detects the first photoacoustic waves that are generated in the subject due to the irradiation of laser light (Step B3). The AD conversion part 22 receives the detection signals of the first photoacoustic waves through the receiving circuit 21, samples the detection signals of the first photoacoustic waves, and stores the detection signals of the first photoacoustic waves in the receiving memory 23. The data separation part 24 transmits the detection signals of the first photoacoustic waves, which are stored in the receiving memory 23, to the photoacoustic image generating part 25, and the photoacoustic image generating part 25 generates the first photoacoustic image on the basis of the detection signals of the first photoacoustic waves (Step B4). The steps, which have been described so far, may be the same as those of the operation procedure (see FIG. 6) described in the first embodiment.

The control part 28 sends a laser oscillation trigger signal to the laser unit 16 that is the second light source. The laser unit 16 excites a laser medium by turning on an excitation light source, such as a flash lamp, in response to the laser oscillation trigger signal, and then emits pulsed laser light by turning on the Q-switch. The relatively large area of the subject is irradiated with the laser light, which is emitted from the laser unit 16, by the probe 11 or the like (Step B5).

The probe 11 detects the second photoacoustic waves that are generated due to the irradiation of laser light of Step B5 (Step B6). The AD conversion part 22 receives the detection signals of the second photoacoustic waves through the receiving circuit 21, samples the detection signals of the second photoacoustic waves, and stores the detection signals of the second photoacoustic waves in the receiving memory 23. The data separation part 24 transmits the detection signals of the second photoacoustic waves, which are stored in the receiving memory 23, to the photoacoustic image generating part 25, and the photoacoustic image generating part 25 generates the second photoacoustic image on the basis of the detection signals of the second photoacoustic waves (Step B7).

The control part 28 sends an ultrasonic trigger signal to the transmission control circuit 29, and the transmission control circuit 29 causes ultrasonic waves to be transmitted from the probe 11 in response to the ultrasonic trigger signal (Step B8). The probe 11 detects reflected ultrasonic waves after transmitting the ultrasonic waves (Step B9). The AD conversion part 22 receives the detection signals of the reflected ultrasonic waves through the receiving circuit 21, samples the detection signals of the reflected ultrasonic waves, and stores the detection signals of the reflected ultrasonic waves in the receiving memory 23. The data separation part 24 transmits the detection signals of the reflected ultrasonic waves, which are stored in the receiving memory 23, to the ultrasound image generating part 26. The ultrasound image generating part 26 generates an ultrasound image on the basis of the detection signals of the reflected ultrasonic waves (Step B10). Steps, which are performed up to the generation of the ultrasound image from the transmission of the ultrasonic waves, may be the same as those of the operation procedure described in the first embodiment.

The image combining part 27 combines the first photoacoustic image generated in Step B4, the second photoacoustic image generated in Step B7, and the ultrasound image generated in Step B10 (Step B11). A composite image formed in Step B11 is displayed on the image display part 14 (Step B12).

Meanwhile, the irradiation of the light emitted from the laser unit 13 as the first light source and the irradiation of the light emitted from the laser unit 16 as the second light source have been separately performed in the above description, but may be performed at the same time. In that case, the probe 11 detects the first photoacoustic waves, which are caused by the irradiation of light emitted from the laser unit 13 as the first light source, and the second photoacoustic waves, which are caused by the irradiation of light emitted from the laser unit 16 as the second light source, at the same time (at one time). In this case, since the generation of a photoacoustic image is completed in one shot, it is possible to display an image in a short time in comparison with a case in which two photoacoustic images are generated and are then combined (superimposed) with each other.

In this embodiment, the subject is irradiated with the light emitted from the laser unit 16 as the second light source, the second photoacoustic waves are detected, and the second photoacoustic image is generated. It is possible to make an image of the distribution of a light absorber, such as blood, with reference to the second photoacoustic image. The tip portion of the puncture needle 15 is irradiated with the light emitted from the laser unit 13, which is the first light source, in addition to the irradiation of the light emitted from the laser unit 16, and photoacoustic waves are generated from the tip portion of the puncture needle 15. Accordingly, even when the tip of the puncture needle 15 is present at a deep portion where the light emitted from the laser unit 16 does not reach, it is possible to confirm the position of the tip of the puncture needle in the photoacoustic image.

Subsequently, a sixth embodiment of the invention will be described. In this embodiment, a puncture needle further includes an inner needle that seals at least a part of an inner cavity of a puncture needle body. The inner needle has an outer diameter that is substantially equal to an inner diameter of the puncture needle body forming, for example, an outer needle, and is adapted to be capable of being separated from and inserted into the hollow puncture needle body. The inner needle is made of a material having light absorbency, for example, a black resin. A light guide member is embedded in the inner needle. The inner needle, particularly, the tip portion of the inner needle also functions as a light absorbent member that absorbs the light emitted from the light emitting portion of the light guide member and generates acoustic waves. The structure of the entire photoacoustic image generating device may be the same as that of the photoacoustic image generating device according to the first embodiment illustrated in FIG. 1, and may be the same as that of the photoacoustic image generating device according to the fifth embodiment illustrated in FIG. 10.

FIG. 13 illustrates the section of a portion of the puncture needle in the vicinity of the tip of the puncture needle that is used in this embodiment. The puncture needle 15c includes an inner needle 158 provided in a hollow puncture needle body 151 that includes an opening at the tip thereof formed at an acute angle and includes an inner cavity therein. The inner needle 158 is made of, for example, a black polyamide resin or a fluorine resin such as PTFE (polytetrafluoroethylene). The tip of the inner needle 158 is formed at an acute angle like the tip of the puncture needle body 151. The light guide member 152 is embedded in the inner needle 158. For example, the light guide member 152 is disposed in a tube that has an inner diameter equal to the inner diameter of the puncture needle body 151, the tube is filled with the black polyamide resin, a fluorine resin, or the like, and the tip portion of the tube is cut, so that the inner needle 158 including the light guide member 152 therein can be produced. The light emitted from the light emitting portion 153 of the light guide member 152 is applied to the tip portion of the inner needle 158 having light absorbency, so that photoacoustic waves are generated at the tip portion of the inner needle 158. The generated photoacoustic waves are detected by the probe 11 (see FIG. 1). A position at which the light guide member 152 is embedded in the inner needle 158 is not particularly limited. The light guide member 152 may be positioned in the vicinity of the center of the inner needle 158, and may be positioned close to the inner wall of the puncture needle body 151 as illustrated in FIG. 2.

FIG. 14A illustrates the appearance of the puncture needle 15c according to this embodiment, FIG. 14B illustrates the appearance of the puncture needle body 151, and FIG. 14C illustrates the appearance of the inner needle 158. The puncture needle body 151 forming the outer needle is mounted on an outer needle base 156 (see FIG. 14B), and the inner needle 158 is bonded to an inner needle base 159 (see FIG. 14C). The inner needle 158 is inserted into the inner cavity of the puncture needle body 151 from the outer needle base 156, and seals at least a part of the inner cavity of the puncture needle body 151 so as to prevent a section or the like of a living body from entering the inner cavity. The inner needle base 159 is provided with a protrusion for connection position alignment, and the outer needle base 156 is provided with a groove that engages with the protrusion of the inner needle base 159. When the inner needle 158 is set to be in the puncture needle body 151, the inner needle base 159 is fitted to the outer needle base 156 after the position of the protrusion of the inner needle base 159 is aligned with the position of the groove of the outer needle base 156.

An operator inserts the puncture needle 15c into the subject while the inner needle 158 is set in the puncture needle body 151 (see FIG. 14A). Since the inner cavity of the puncture needle body 151 is closed by the inner needle 158, it is possible to prevent flesh from being caught while the needle is inserted. Accordingly, it is possible to prevent the deterioration of an operator's feeling during inserting a needle. Further, it is also possible to prevent water from flowing into the inner cavity of the puncture needle body 151 from a puncture portion. The operator releases the connection between the inner needle base 159 and the outer needle base 156 after inserting the needle into the subject, and removes the inner needle 158 from the puncture needle body 151. After removing the inner needle 158, the operator mounts a syringe or the like on the outer needle base 156 and injects a drug such as an anesthetic. Alternatively, the operator takes a biopsy tissue sample from a portion of the subject into which the puncture needle 15c is inserted.

FIG. 15 illustrates the connection between the laser unit 13 and the puncture needle 15c. For example, a laser diode light source is used as the laser unit 13. The laser diode light source, a drive circuit therefor, and the like are housed in a box that has a width of about 125 mm, a depth of about 70 mm, and a height of about 40 mm. Direct current (DC) power is supplied to the laser unit 13 from a universal serial bus (USB) terminal that is provided in, for example, an ultrasonic unit. The pulse energy of pulsed laser light emitted from the laser unit 13 is, for example, 0.006 mJ, and the pulse width of the pulsed laser light is in the range of, for example, 60 ns to 100 ns. The number of times of repetition (frequency) of the pulsed laser light per unit time is equal to or higher than, for example, 30 Hz.

An optical fiber 30 is used to guide light to the puncture needle 15c from the laser unit 13. The optical fiber 30 includes an optical connector 31 at the tip thereof (an end of the optical fiber 30 distant from the laser unit 13 when view from the laser unit 13). The inner needle base 159 of the puncture needle 15c is provided with an optical connector that connects the optical connector 31. The light guided by the optical fiber 30 is incident on the light guide member 152 (see FIG. 13), which is provided in the inner needle 158, from the optical connector 31, and is applied to the tip portion of the inner needle 158 from the light emitting portion 153. When the inner needle base 159 is provided with the optical connector, the optical fiber 30 guiding the light emitted from the laser unit 13 to the inner needle and the inner needle section can be separated from each other and handled. Accordingly, an inner needle section including the inner needle 158 and the inner needle base 159 can be sterilized and then packed. In order to use the inner needle section, an operator has only to take the inner needle section out of a sterilizing bag and connect the optical connector of the inner needle base 159 to the optical connector 31 of the optical fiber 30.

Meanwhile, an example in which the inner needle base 159 is provided with the optical connector has been described above. However, the inner needle base 159 may not be provided with the optical connector, the puncture needle 15c may also be provided with an optical fiber extending from the inner needle base 159, and an optical connector may be provided at the tip of the optical fiber. In this case, the optical fiber, which extends from the inner needle base 159, and the inner needle section may be sterilized and packed together. When the inner needle base 159 is provided with an optical connector, the weight of the inner needle base 159 is increased by as much as the weight of the optical connector in comparison with a case in which the optical connector is not provided. Since the weight balance of the puncture needle 15c is poor when the inner needle base 159 is excessively heavy, it is considered that it is difficult to handle the puncture needle 15c. In such a case, an optical connector may be provided at a position away from the inner needle base 159.

The optical fiber extending from the inner needle base 159 may not be provided with an optical connector, and the end face of the optical fiber may be polished so as to be capable of guiding light or the end face of the optical fiber may be cut smoothly. In that case, the tip of the optical fiber extending from the inner needle base 159 is inserted into the laser unit 13 and a receptacle for pressing the inserted optical fiber by a spring force may be provided. In this case, since the optical fiber is separated from the receptacle when a force equal to or larger than a predetermined force is applied to the optical fiber, the breakage of the optical fiber, which is caused by the application of an excessive force, does not occur. Further, since a connector (plug) does not need to be mounted on the optical fiber extending from the inner needle base 159, it is possible to reduce the costs of the puncture needle.

In this embodiment, the puncture needle 15c includes the inner needle 158. Since the inner cavity of the puncture needle body 151 forming the outer needle is closed by the inner needle 158, an operator can insert the puncture needle 15c into the subject without the deterioration of a feeling during inserting the needle. Furthermore, it is possible to prevent water and the like from flowing backward in the inner cavity of the puncture needle body 151. In this embodiment, the inner needle is made of a material having light absorbency and the light guide member 152 is provided in the inner needle 158. Since light is guided to the tip portion of the puncture needle by the light guide member 152 and is applied to the tip portion of the inner needle 158 from the light emitting portion 153, photoacoustic waves are generated at the tip portion of the inner needle 158 and the tip of the puncture needle can be made visible by a photoacoustic image.

Next, a seventh embodiment of the invention will be described. In the sixth embodiment, the light guide member 152 has been disposed in the inner needle 158 (see FIG. 13). In this embodiment, a light guide member 152 is used as an inner needle that seals at least a part of an inner cavity of a puncture needle body 151. Further, at least a part of a light guide member 152, which includes a light emitting portion 153, is covered with a film having light absorbency, for example, a black fluorine resin. Other structures are the same as those of the sixth embodiment.

FIG. 16 illustrates the appearance of the inner needle that is used in the puncture needle of this embodiment. The light guide member 152 has an outer diameter that is substantially equal to the inner diameter of the hollow puncture needle body 151. An optical fiber having a core diameter of, for example, about 400 µm is used as the light guide member 152. A total diameter of the light guide member 152 and the clad or the coating thereof is about 550 µm. The inner needle includes a black fluorine resin film 160 at a part of the light guide member 152 including the tip thereof. The inner needle has only to include the black fluorine resin film 160 on at least the tip of the light guide member 152, and may include a black fluorine resin film over the entire light guide member 152 in a longitudinal direction.

FIG. 17 illustrates the section of the tip portion of the inner needle. Since the inner needle includes the black fluorine resin film 160, which has light absorbency, at the tip portion of the light guide member 152, the light emitting portion 153 of the light guide member 152 is covered with the black fluorine resin film 160. Light emitted from the light emitting portion 153 is absorbed by the black fluorine resin film 160, so that photoacoustic waves are generated at the tip portion of the inner needle 158. The generated photoacoustic waves are detected by the probe 11 (see FIG. 1).

In this embodiment, the light guide member 152 is used as the inner needle and the inner cavity of the puncture needle body 151 is closed by the light guide member 152. In this embodiment, the light guide member 152 closes the inner cavity of the puncture needle body 151 unlike in the sixth embodiment. Accordingly, an optical fiber having a diameter, which is larger than that in the sixth embodiment, can be used as the light guide member 152. Other effects are the same as those of the sixth embodiment.

Further, an eighth embodiment of the invention will be described. FIG. 18 illustrates the section of an inner needle that is used in the eighth embodiment of the invention. In this embodiment, the inner needle includes a tube 161, a light guide member 152, and a light absorbent member 154. The tube 161, the light guide member 152, and the light absorbent member 154 form the inner needle that is inserted into an inner cavity of a puncture needle body. Although not illustrated in FIG. 18, the tube 161 and the light guide member 152 are bonded to the inner needle base 159 (see FIG. 14C). The tube 161, the light guide member 152 and the light absorbent member 154 are inserted into the inner cavity of the puncture needle body 151 from the outer needle base 156 (see FIG. 14B). Other structures are the same as those of the sixth embodiment.

The tube 161 is a hollow tube that houses the light guide member 152 therein. The tube 161 is made of a fluorine resin such as PTFE. The light guide member 152 is an optical Liber having a core diameter of, for example, 200 μm, and the outer diameter of the tube 161 is, for example, 406 μm. The light absorbent member 154 is disposed at the tip of the tube 161. The light absorbent member 154 is cut at an acute angle like the tip of the puncture needle that is formed at an acute angle. An epoxy resin, a polyurethane resin, a fluorine resin, silicone rubber, or the like, into which a black pigment having light absorbency is mixed, can be used for the light absorbent member 154. A void is present between a light emitting portion 153 of the light guide member 152 and the light absorbent member 154. In other words, the light emitting portion 153 of the light guide member 152 and the light absorbent member 154 face each other with an air layer interposed therebetween.

Light emitted from the laser unit 13 (see FIG. 15) is guided to the vicinity of the tip of the puncture needle (inner needle) by the light guide member 152, and is applied to the light absorbent member 154 from the light emitting portion 153 through the void. When the light absorbent member 154 absorbs the light to be applied, photoacoustic waves are generated at the tip portion of the puncture needle. At this time, since the acoustic impedance of the light absorbent member 154 is closer to that of biological tissue than that of air, most of photoacoustic waves generated by the light absorbent member 154 are emitted to the outside from the opening of the puncture needle. Since an air layer is provided on the back side of the light absorbent member 154, the photoacoustic waves generated by the light absorbent member 154 can be efficiently emitted to the outside from the front.

Subsequently, a ninth embodiment of the invention will be described. FIG. 19 illustrates the section of a portion of a puncture needle in the vicinity of the tip of the puncture needle that is used in the ninth embodiment of the invention. The puncture needle 15d of this embodiment includes a puncture needle body 151, a tube 161, a transparent resin 163, a light guide member 152, and a light absorbent member 154. The tube 161, the transparent resin 163, the light guide member 152, and the light absorbent member 154 form an inner needle 158 that is inserted into an inner cavity of the puncture needle body 151. Although not illustrated in FIG. 19, the tube 161 and the light guide member 152 are bonded to the inner needle base 159 (see FIG. 14C). The inner needle 158 is inserted into the inner cavity of the puncture needle body 151 from the outer needle base 156 (see FIG. 14B). Other structures are the same as those of the sixth embodiment.

The tube 161 is a hollow tube that is made of, for example, polyimide. The tube 161 may be a tube that is made of metal such as stainless steel. The transparent resin 163 is disposed in the tube 161. For example, an epoxy resin (adhesive) is used as the transparent resin 163. The transparent resin 163 has only to cover at least a tip portion of the tube 161, and does not necessarily need to cover the entire inside of the tube 161. A photocurable resin, a thermosetting resin, or a room temperature-curable resin can be used as the transparent resin 163.

The light guide member 152 is embedded in the tube 161 by the transparent resin 163. A light emitting end of the light guide member 152 forms the light emitting portion 153. The tip portion of the tube 161 includes the light absorbent member 154, and the light absorbent member 154 is irradiated with the light emitted from the light emitting portion 153. For example, an epoxy resin, a polyurethane resin, a fluorine resin, silicone rubber, or the like, into which a black pigment is mixed, can be used for the light absorbent member 154.

The inner needle 158 used in this embodiment can be produced by the following procedure. First, the transparent resin 163, which is not yet cured, is injected into the tube 161. After that, the light guide member 152 is inserted into the tube 161, and the light emitting end of the light guide member 152 forming the light emitting portion 153 is positioned so as to be disposed in the vicinity of the tip portion of the tube 161. In the positioning of the light emitting end, the light guide member 152 is observed using, for example, a microscope or the like and the position of the light emitting end of the light guide member 152 may be adjusted so that the light emitting end of the light guide member 152 is disposed at the tip portion of the tube 161. Since the transparent resin 163 has transparency, it is possible to confirm the position of the light emitting end of the light guide member 152 during the adjustment of the position of the light emitting end of the light guide member. Instead, the light guide member 152 is inserted first and the transparent resin 163 is then injected.

After being positioned, the transparent resin 163 is cured by, for example, thermal curing while the light guide member 152 is inserted into the tube 161. Then, the tips of the tube 161 and the transparent resin 163 are cut at an acute angle so as to have a shape suitable for the tip of the puncture needle body 151. Subsequently, a resin, which forms the light absorbent member 154 and has light absorbency, is applied so as to cover at least a part of the cut surfaces of the tube 161 and the transparent resin 163, and the resin is cured by, for example, thermal curing.

After the light guide member 152 is inserted into the tube 161, the position of the light guide member 152 is adjusted, and the transparent resin is cured, the tube is cut at an acute angle in the above description. However, the invention is not limited thereto. After the tube is cut at an acute angle first, the light guide member 152 is inserted into the tube, and the position of the light guide member 152 is adjusted, the transparent resin may be cured. In this case, a metal tube may be used as the tube.

In this embodiment, the tube 161 and the transparent resin 163 form the inner needle 158 and the light guide member 152 is embedded in the tube 161 by the transparent resin 163. Since the transparent resin 163 is used, it is possible to visually confirm the position of the tip of the light guide member 152 during the embedment of the light guide member 152. Accordingly, it is possible to dispose the light emitting portion 153 at a position that as close to the tip of the inner needle 158 as possible.

Further, in this embodiment, the light absorbent member 154 is disposed on the surface of the tip portion of the inner needle 158. Light emitted from the light emitting portion 153 of the light guide member 152 is applied to the light absorbent member 154 through the transparent resin 163, so that photoacoustic waves are generated from the light absorbent member 154. Since the photoacoustic waves are generated at the surface of the tip portion of the inner needle 158, attenuation factors are less. Accordingly, it is possible to stably detect the photoacoustic waves. Furthermore, since light is applied through the transparent resin 163, it is possible to apply light to the light absorbent member 154 even though the position of the light emitting portion 153 deviates to some extent.

The inventor performed experiments to confirm whether or not an image of the position of a tip of a needle could be made in a photoacoustic image after an inner needle 158 in which an optical fiber having a core diameter of 200 μm was used as the light guide member 152 was produced, the inner needle 158 was mounted on a block needle having a thickness of 22 G (gauge), and the block needle was inserted at an insertion angle of 80°. Pulsed laser light, which had a pulse energy of 6.4 μJ at a pulse width of 80 ns, was emitted from a light source; light was applied to a black epoxy resin, which was provided on the surface of the tip portion of the inner needle 158, from the optical fiber; and photoacoustic waves generated from the black epoxy resin were detected by a linear probe having a center frequency of 6.5 MHz. When the photoacoustic waves were formed into an image, it was possible to confirm that an image could be formed even when the puncture needle was inserted to a position corresponding to a depth of 77 mm. Further, it was confirmed that an image of the position of the tip of the needle could be more clearly formed by averaging detection results of eight times. Furthermore, it was confirmed that an image could be formed at a position corresponding to a depth of 78 mm when light, which had a pulse energy of 2.0 μJ at a pulse width of 80 ns, was emitted from the light source, even though an optical fiber having a core diameter of 100 μm was used as the light guide member 152.

Subsequently, a tenth embodiment of the invention will be described. FIG. 20 illustrates the section of a portion of a puncture needle in the vicinity of the tip of the puncture needle that is used in the tenth embodiment of the invention. The puncture needle 15e of this embodiment includes a puncture needle body 151, a tube 161, a transparent resin 163, a light guide member 152, and a light absorbent member 154. The puncture needle 15e of this embodiment is different from the puncture needle 15d of the ninth embodiment illustrated in FIG. 19 in that the light absorbent member 154 covers a light emitting portion 153 and is embedded in the transparent resin 163 together with the light guide member 152. Other structures are the same as those of the ninth embodiment.

An inner needle 158 used in this embodiment can be produced by the following procedure. First, a light-absorbent resin is attached so as to cover at least a part of a light emitting end of the light guide member 152 that forms the light emitting portion 153. For example, an epoxy resin, a polyurethane resin, a fluorine resin, silicone rubber, or the like, into which a black pigment is mixed, can be used as the light-absorbent resin. After that, the light-absorbent resin is cured by, for example, thermal curing. The light-absorbent resin forms the light absorbent member 154.

Subsequently, the light guide member 152, which includes the light absorbent member 154 attached to the tip portion thereof, is inserted into the tube 161, and the light emitting end of the light guide member 152 forming the light emitting portion 153 is positioned so as to be disposed in the vicinity of the tip portion of the tube 161. In the positioning of the light emitting end, the light guide member 152 is observed using, for example, a microscope or the like and the position of the light emitting end of the light guide member 152 may be adjusted so that the light emitting end of the light guide member 152 is disposed at the tip portion of the tube 161.

Subsequently, a transparent resin 163, which is not yet cured, is injected into the tube 161, and the transparent resin 163 is cured by, for example, thermal curing while the light guide member 152 is inserted into the tube 161. For example, a soft epoxy resin, in which the attenuation of acoustic waves is less, may be used as the transparent resin 163. After that, the tips of the tube 161 and the transparent resin 163 are cut at an acute angle so as to have a shape suitable for the tip of the puncture needle body 151. Instead, the light guide member 152 is inserted first and the transparent resin 163 is then injected.

After the light guide member 152, which includes the light absorbent member 154 attached to the tip portion thereof, is inserted into the tube 161 and the position of the light guide member 152 is adjusted, the tube 161 is cut at an acute angle in the above description. However, the invention is not limited thereto. The tip of the tube 161 may be cut at an acute angle first; the light guide member 152, which includes the light absorbent member 154 attached to the tip portion thereof, may be inserted into the tube; and the position of the light guide member 152 may be adjusted. In this case, a metal tube may be used as the tube 161.

In this embodiment, the light absorbent member 154 is provided at the light emitting end of the light guide member 152 forming the light emitting portion 153, and the light guide member 152 and the light absorbent member 154 are embedded in the transparent resin 163. In this embodiment, it is possible to reduce the volume of the light absorbent member 154 and to make a source, which generates photoacoustic waves, be close to a point sound source in comparison with the ninth embodiment. Other effects are the same as those of the ninth embodiment.

The inventor performed experiments to confirm whether or not an image of the position of a tip of a needle could be made in a photoacoustic image after an inner needle 158 in which an optical fiber having a core diameter of 200 μm was used as the light guide member 152 was produced, the inner needle 158 was mounted on a needle having a thickness of 22 G (gauge), and the needle was inserted at an insertion angle of 80°. Pulsed laser light, which had a pulse energy of 6.4 μJ at a pulse width of 80 ns, was emitted from a light source; light was applied to a black epoxy resin that was provided on the surface of the tip portion of the optical fiber; and photoacoustic waves generated from the black epoxy resin were detected by a probe. When the photoacoustic waves were formed into an image, it was possible to confirm that an image could be formed even when the puncture needle was inserted to a position corresponding to a depth of 77 mm. Further, it was confirmed that an image of the position of the tip of the needle could be more clearly formed by the averaging of detection results of eight times. Furthermore, it was confirmed that an image could be formed at a position corresponding to a depth of 78 mm when light, which had a pulse energy of 2.0 µJ at a pulse width of 80 ns, was emitted from the light source, even when an optical fiber having a core diameter of 100 µm was used as the light guide member 152.

Meanwhile, it has been described that the probe 11 detects both the photoacoustic waves and the reflected ultrasonic waves in each of the above-mentioned embodiments. However, a probe used to generate an ultrasound image does not necessarily need to be the same as a probe used to generate a photoacoustic image. The photoacoustic waves and the reflected ultrasonic waves may be detected by separate probes. Further, any one of the detection (sampling) of the photoacoustic waves and the detection (sampling) of the reflected ultrasonic waves may be performed first.

Since the refractive index of water, air, or the like present in the puncture needle 15 is lower than the refractive index of the optical fiber in the third embodiment, the light emitting end face of the optical fiber is formed obliquely so that a portion of the puncture needle close to the inner wall (a portion opposite to the center of the puncture needle) is long. When the puncture needle is filled with a material having a refractive index higher than the refractive index of the optical fiber, the end face of the optical fiber close to the light emitting end may be formed obliquely so that a portion of the puncture needle close to the center (a portion opposite to the inner wall) is long in contrast to FIG. 9.

The laser unit 13 and the laser unit 16 have been described as independent light sources in the fifth embodiment, but one light source may also function as the other light source. FIG. 21 illustrates a modification of light sources of first and second light sources used in the photoacoustic image generating device according to the fifth embodiment. In the modification illustrated in FIG. 21, a laser unit 16, which is the second light source, also functions as the first light source. A part of laser light emitted from the laser unit 16 is brandied toward a subject, and at least a part of the rest of the laser light is branched toward a puncture needle 15. A branch ratio can be set to, for example, about 100:1.

For example, after light emitted from the laser unit 16 is diffused by a diffusion plate 17, the light is incident on a bundle fiber 19, which is formed of, for example, about 100 optical fibers having been bundled, through a condensing lens 18. It is possible to suppress the variation of the intensity of the light, which is incident on the bundle fiber 19, by the diffusion plate 17 and the condensing lens 18. A part of the bundle fiber 19, for example, one optical fiber is branched toward the puncture needle 15, and the rest thereof are brandied toward the subject. For example, the probe may be provided with an optical connector that connects the optical fibers extending from the puncture needle 15. Further, after all light is guided to the probe by the bundle fiber 19, a part of the guided light may be branched toward the puncture needle in the probe. Meanwhile, a method of branching light is not limited to the above-mentioned method, and may be other methods of branching light, such as a method using a beam splitter that transmits most of light and reflects a part of the light, or the like. In this case, it is preferable that a connector to be connected to a light guide member extending from a puncture needle is provided on a laser system.

Examples in which the tube 161, the light guide member 152, and the light absorbent member 154 are used as the inner needle have been described in the eighth to tenth embodiments, but the invention is not limited thereto. The diameter of the tube 161 may be set to be smaller than the inner diameter of the puncture needle body 151, and the tube 161 may be disposed along the inner cavity of the puncture needle body 151 as in FIG. 2. The respective effects are maintained even in this case.

The puncture needle is not limited to a needle that is to be percutaneously inserted into a subject from the outside of the subject, and may be a needle for an ultrasonic endoscope. The needle for an ultrasonic endoscope may be provided with a light guide member 152 and a light absorbent member 154, the light absorbent member 154 provided at the tip portion of the needle may be irradiated with light, and photoacoustic waves may be detected to generate a photoacoustic image. In this case, it is possible to insert the needle while observing the photoacoustic image to confirm the position of the tip portion of the needle for an ultrasonic endoscope. The photoacoustic waves, which are generated at the tip portion of the needle for an ultrasonic endoscope, may be detected by a probe for a body surface and may be detected by a probe assembled in the endoscope.

The light guide member 152, such as an optical fiber, may be fixed to an inner wall in an inner cavity of an insertion object, such as a puncture needle, by an adhesive. Alternatively, a hollow tube, which has a diameter smaller than the diameter of the inner cavity, is inserted into the inner cavity of the insertion object, and the light guide member 152 may be fixed by the tube. FIG. 22A is a perspective view of a puncture needle and FIG. 22B illustrates a section taken along line A-A of FIG. 22A. As illustrated in FIG. 22A, the puncture needle 15f includes a tube 162 in a puncture needle body 151. As illustrated in FIG. 22B, a light guide member 152 is held between an inner cavity of the puncture needle body 151 and the tube 162. The outer diameter of the tube 162 is smaller than the inner diameter of the puncture needle body 151 by the outer diameter of the light guide member 152.

In the assembly of the puncture needle 15f, the light guide member 152 is inserted into the inner cavity of the puncture needle 15f first and the tube 162 is then inserted into the inner cavity of the puncture needle body 151. The light guide member 152 is pressed against the inner wall of the puncture needle body 151 by the inserted tube 162, so that the light guide member 152 is fixed in the inner cavity of the puncture needle body 151. The tube 162 keeps the light guide member 152 at a predetermined position in the inner cavity by a frictional force between itself and the inner wall of the puncture needle body 151. In addition, the inner cavity of the puncture needle body 151 and the tube 162 may be bonded to each other by an adhesive.

For example, a metal, a fluorine resin, polyimide, or the like can be used as a material of the tube 162. When a metal such as stainless steel is used as the material of the tube 162, the light guide member 152 can be reliably held. When a fluorine resin is used as the material of the tube 162, the thickness (wall thickness) of the tube can be reduced and the flow rate of a medicinal solution or the like can be increased in comparison with a case in which a metal is used as the material of the tube 162. When polyimide is used as the material of the tube 162, the tube 162 can be easily inserted into the puncture needle body 151 since polyimide is hard.

Accordingly, it is easy to assemble the tube 162. Further, the thickness of the tube can be reduced and the flow rate of a medicinal solution or the like can be increased. Meanwhile, additives and the like may be added to the respective materials.

Light emitted from the light guide member 152 is applied to the light absorbent member 154 provided in the vicinity of the tip of the puncture needle body 151, so that photoacoustic waves are generated from the light absorbent member 154. As in the third embodiment, the light absorbent member 154 may also function as a fixing member for fixing the tip portion of the light guide member to the inner wall of the puncture needle body 151. Alternatively, at least the tip portion of the light guide member 152 may be covered with a resin having light absorbency.

The puncture needle has been considered as an insertion object in each of the above-mentioned embodiments, but the insertion object is not limited thereto. The insertion object may be a radiofrequency cauterization needle that houses electrodes used in radiofrequency cauterization, may be a catheter that is to be inserted into a blood vessel, and may be a guide wire for a catheter that is to be inserted into a blood vessel. Alternatively, the insertion object may be an optical fiber for laser treatment.

FIG. 23 illustrates an example of a radiofrequency cauterization needle. The radiofrequency cauterization needle 250 includes a light guide member 152 and a light absorbent member 154. The radiofrequency cauterization needle 250 is used in radiofrequency cauterization for liver cancer, breast cancer, or the like. A doctor or the like inserts the radiofrequency cauterization needle 250 into a subject so that the tip of the radiofrequency cauterization needle (handpiece) 250 is disposed at a desired position. At this time, electrodes (deployment needles) 251 are housed in the radiofrequency cauterization needle 250. When the radiofrequency cauterization needle 250 is inserted into the subject, light is emitted from the laser unit 13 (see FIG. 1) and is applied to the light absorbent member 154 from the light guide member 152. Photoacoustic waves, which are generated when the light absorbent member 154 absorbs light, are detected by the probe 11 (see FIG. 1), so that a photoacoustic image is generated. With reference to the photoacoustic image, it is possible to confirm the position of the tip of the radiofrequency cauterization needle 250 and to dispose the tip of the needle at an accurate position in a lesioned part to be cauterized. After the tip of the radiofrequency cauterization needle 250 is disposed at the desired position, electrodes 251 are made to protrude from the radiofrequency cauterization needle 250, and a target portion is irradiated with radio waves having a frequency of, for example, about 500 KHz.

FIG. 24 illustrates another example of the radiofrequency cauterization needle. In this example, a light guide member 257 for an electrode and a light absorbent member 259 for an electrode are also mounted on a needle-like electrode 251. The light guide member 257 for an electrode guides light emitted from the laser unit 13 (see FIG. 1). The light emitting portion 258 for an electrode is provided in the vicinity of the tip portion of the electrode 251, and emits the light that is guided by the light guide member 257 for an electrode. The light absorbent member 259 for an electrode generates photoacoustic waves that are caused by the light emitted from the light emitting portion 258 for an electrode. In the example of FIG. 24, photoacoustic waves are generated at two portions, that is, the tip of the radiofrequency cauterization needle 250 and the tip of the electrode 251.

After the radiofrequency cauterization needle 250 is inserted at a desired position, the electrode 251 is made to protrude from the radiofrequency cauterization needle 250. The example of FIG. 24 is the same as the example of FIG. 23 in that light is emitted from the laser unit 13, when the radiofrequency cauterization needle 250 is inserted at a desired position, and the position of the tip of the radiofrequency cauterization needle 250 can be confirmed using a photoacoustic image. After the electrode 251 is made to protrude, light is emitted from the laser unit 13 and is applied to the light absorbent member 154 provided at the tip of the radiofrequency cauterization needle 250 and the light absorbent member 259 for an electrode provided at the tip of the electrode 251. The photoacoustic waves generated at the tip of the radiofrequency cauterization needle 250 and the photoacoustic waves generated at the tip of the electrode 251 are detected by the probe 11, so that a photoacoustic image is generated. It is possible to confirm a range (cauterization range), which is irradiated with radio waves, with reference to this photoacoustic image.

FIG. 25 illustrates a catheter. The catheter 253 is used for treatment in a blood vessel, for example, percutaneous transluminal coronary angioplasty and the like. Specifically, the catheter 253 is a guiding catheter. The catheter 253 is not limited to a guiding catheter, and may be a balloon catheter. The light guide member 152 is inserted into the catheter 253, and guides light, which is emitted from the laser unit 13 (see FIG. 1), to the tip portion of the catheter 253. The light absorbent member 154 is disposed in the vicinity of the tip of the catheter 253. A doctor or the like inserts the catheter 253 into a blood vessel so that the tip of the catheter 253 is disposed at a desired position. At that time, light is emitted from the laser unit 13 and is applied to the light absorbent member 154 that is disposed in the vicinity of the tip of the catheter 253 through the light guide member 152. Photoacoustic waves, which are generated when the light absorbent member 154 absorbs light, are detected by the probe 11, so that a photoacoustic image is generated. It is possible to confirm the position of the tip of the catheter 253 with reference to this photoacoustic image during the insertion of the catheter 253.

FIG. 26 illustrates a guide wire. The guide wire 254 is a wire that guides a catheter used for treatment in a blood vessel. The light guide member 152 is attached to the guide wire 254 along the guide wire 254 and guides light, which is emitted from the laser unit 13 (see FIG. 1), to the tip portion of the guide wire 254. The light guide member 152 may be inserted into the guide wire 254 instead of being attached to the outside of the guide wire 254. The light absorbent member 154 is disposed in the vicinity of the tip of the guide wire 254. A doctor or the like inserts the guide wire 254 into a blood vessel so that the tip of the guide wire 254 is disposed at a desired position. At that time, light is emitted from the laser unit 13 and is applied to the light absorbent member 154 that is disposed in the vicinity of the tip of the guide wire 254 through the light guide member 152. Photoacoustic waves, which are generated when the light absorbent member 154 absorbs light, are detected by the probe 11, so that a photoacoustic image is generated. It is possible to confirm the position of the tip of the guide wire 254 with reference to this photoacoustic image during the insertion of the guide wire 254.

FIG. 27 illustrates an example of an optical fiber for laser treatment. The optical fiber 255 is an optical fiber that is used to treat varicose veins, to break a stone, and the like. In this example, the optical fiber 255 also functions as a light guide member for guiding light, which is emitted from the laser unit 13 (see FIG. 1), to the tip portion of an insertion object. The light absorbent member 154 is disposed at the tip of the optical fiber 255. FIG. 28 illustrates another example of the optical fiber for laser treatment. In this example, the tip of the optical fiber 255 is sealed by a cap 256. In this case, the light absorbent member 154 may be disposed at the tip of the cap 256.

A doctor or the like inserts the optical fiber 255 into a subject so that the tip of the optical fiber 255 is disposed at a desired position. At that time, light is emitted from the laser unit 13 and is applied to the light absorbent member 154 that is disposed in the vicinity of the tip of the cap 256 through the optical fiber 255. Photoacoustic waves, which are generated when the light absorbent member 154 absorbs light, are detected by the probe 11, so that a photoacoustic image is generated. It is possible to confirm the position of the tip of the optical fiber 255 with reference to this photoacoustic image. After the optical fiber 255 is disposed at a desired position, laser light for treatment may be emitted from the optical fiber 255 by the switching of a light source, or the like.

A needle, which includes an opening at the tip thereof, has been assumed as the needle in each of the above-mentioned embodiments, but the opening does not necessarily need to be provided at the tip portion of the needle. The needle is not limited to a needle such as an injection needle, and may be a biopsy needle that is used for biopsy. That is, the needle may be a biopsy needle that is inserted into an inspection object of a living body and can take the tissue of a biopsy region of the inspection object. Further, the needle may be used as a guiding needle that is used for the insertion of a needle to a deep portion, such as an organ under the skin or in the abdominal cavity, FIG. 29 illustrates the section of a tip portion of a biopsy needle. The biopsy needle 164 includes a collecting portion (suction port) 165 that is formed on the side surface thereof and is used to take the tissue of a biopsy region such as calcified tissue by suction. The light guide member 152 is inserted into the biopsy needle 164. A light emitting end of the light guide member 152, which forms a light emitting portion 153, is disposed in the vicinity of the collecting portion 165. Since a light absorbent member 154 is disposed at a position where the light absorbent member 154 covers the light emitting portion 153, it is possible to venerate photoacoustic waves from the position of the collecting portion 165. Accordingly, it is possible to confirm the position of the collecting portion 165 by a photoacoustic image. The light absorbent member 154 may also be provided at the tip portion of the biopsy needle 164, and the light absorbent member 154 may be irradiated with light so that photoacoustic waves are generated at the tip of the biopsy needle 164.

An operator inserts the biopsy needle 164 into a subject and adjusts a insertion position so that the position of the collecting portion 165 is disposed in a biopsy region, while confirming the position of the collecting portion 165 by a photoacoustic image. After the biopsy needle is disposed at a desired position, the tissue of a biopsy region is sucked into the biopsy needle 164 from the collecting portion 165 and the tissue of the biopsy region is excised. Then, the sucked tissue is recovered from the collecting portion 165.

A laser unit having the following structure other than the laser units illustrated in FIGS. 3 and 4 may be used as the laser unit 13. FIG. 30 illustrates still another configuration example of the laser unit. A laser unit 40 includes a power input terminal 41, a trigger input terminal 42, a DC-DC conversion part 43, a pulse laser diode light source 45, a coupling optical system 46, and a light output terminal 47. The laser unit 40 is used as the laser unit 13 illustrated in FIG. 1 or 10. The external dimensions of the laser unit 40 are, for example, length of 74 mm×width of 54 mm×height of 20 mm.

The power input terminal 41 is connected to a power supply line of an ultrasonic unit 12 (see FIGS. 1 and 10). For example, Direct current (DC) power of 5 V is supplied to the power input terminal 41. The trigger input terminal 42 is connected to a signal output line of the ultrasonic unit 12. The power input terminal 41 and the trigger input terminal 42 are formed of, for example, a USB connector. The ultrasonic unit 12 includes a USB port (receptacle). When the USB connector including the power input terminal 41 and the trigger input terminal 42 is inserted into the USB port, power is supplied to the laser unit 40 and signals output from the ultrasonic unit 12 are supplied to the laser unit 40.

The DC-DC conversion part 43 converts the voltage of the DC power that is supplied from the power input terminal 41. The DC-DC conversion part 43 converts, for example, DC 5 V into DC 12 V. A pulse laser diode drive circuit 44 drives the pulse laser diode light source 45. The pulse laser diode light source 45 is driven by DC power that is supplied from the DC-DC conversion part 43. The pulse laser diode drive circuit 44 causes pulsed laser light to be emitted from the pulse laser diode light source 45 at a desired timing by controlling the DC power, which is supplied to the pulse laser diode light source 45, on the basis of a trigger signal input from the trigger input terminal 42.

The coupling optical system 46 couples the pulse laser diode light source 45 to the light output terminal 47. The coupling optical system 46 includes, for example, a condensing lens and the like. In terms of reduction of weight, it is preferable that the pulse laser diode source 45, the coupling optical system 46, and the light output terminal 47 are integrated by welding. An optical fiber 48, which guides light to an insertion object such as a puncture needle 15, is optically connected to the light output terminal 47. The optical fiber 48 is, for example, an optical fiber that forms the light guide member 152 of the puncture needle 15. It is preferable that element wires of the optical fiber 48 can be connected to the light output terminal 47. For example, an FC type bare fiber adapter is used as the light output terminal 47.

FIG. 31 illustrates the appearance of a photoacoustic image generating device including the laser unit 40. A probe 11 is connected to the ultrasonic unit 12. The ultrasonic unit 12 is formed of an integrated unit including image display part 14. Programs for the generation of a photoacoustic image are incorporated into the ultrasonic unit 12. The ultrasonic unit 12 includes a USB port 32. The USB connector, which includes the power input terminal 41 and the trigger input terminal 42 of the laser unit 40, is inserted into the USB port 32. When the USB connector is inserted into the USB port of the ultrasonic unit 12 in a case in which the laser unit 40 is a card-sized, small and light unit, the laser unit 40 can be held.

The puncture needle 15 is not particularly limited, but may be a puncture needle that includes the inner needle described in the sixth to tenth embodiments. Other insertion objects may be used instead of the puncture needle 15. One end of the optical fiber, which forms the light guide member 152 of the puncture needle 15, is connected to the light output terminal 47 of the laser unit 40. The optical fiber is inserted into the light output terminal 47, and is held by a spring force or the like. When an operator pulls the puncture needle 15 and a large force is applied to the light output terminal 47, the optical fiber is separated from the light output terminal 47. Accordingly, it is possible to prevent the optical fiber from being broken. Further, since the optical fiber can be directly separated from and inserted into the light output terminal 47, the optical fiber extending from the puncture needle 15 does not need to be provided with a connector. Accordingly, there is an effect capable of reducing costs.

The pulse energy of pulsed laser light emitted from the laser unit 40 can be 6.4 µJ when the core diameter of the optical fiber forming the light guide member 152 is 200 µm. When the core diameter of the optical fiber is 100 µm, the pulse energy of pulsed laser light can be 2.0 µJ. A pulse time width can be 80 ns. A pulse repetition rate may be 60 Hz when an image is displayed at, for example, 30 fps. The repetition rate can be 3300 Hz at the maximum.

Meanwhile, in FIG. 31, the light output terminal 47 is provided on the surface of the laser unit opposite to the surface of the laser unit on which the USB connector including the power input terminal 41 and the trigger input terminal 42 is present. However, it is preferable that the light output terminal 47 is present on the surface of the laser unit orthogonal to the surface of the laser unit on which the USB connector is present. When an operator moves the puncture needle 15 and the laser unit 40 is pulled in a case in which the USB connector and the light output terminal 47 are provided on the surfaces of the laser unit opposite to each other, the USB connector is separated from the USB port 32. In contrast, when the USB connector and the light output terminal 47 are provided on the surfaces of the laser unit orthogonal to each other, the USB connector is not easily separated from the USB port 32 even if the laser unit 40 is pulled.

The invention has been described above on the basis of the preferred embodiments thereof. However, the photoacoustic image generating device and the puncture needle of the invention are not limited to only the above-mentioned embodiments, and various alterations and modifications formed from the structures of the above-mentioned embodiments are also included in the scope of the invention.

What is claimed is:

1. A photoacoustic image generating device comprising:
   a first light source;
   a needle that is adapted to be inserted into a subject, the needle including:
      a first optical fiber that guides light emitted from the first light source and has a light emitting portion for the light guided by the first optical fiber; and
      a light absorbent member that generates first photoacoustic waves caused by the light emitted from the light emitting portion;
   wherein
      the needle has an opening and an inner cavity therein;
      the needle further has an inner needle that seals at least a part of the inner cavity;
      the inner needle includes a hollow tube and a transparent resin that closes at least a tip portion of the hollow tube;
      the first optical fiber is embedded in the hollow tube by the transparent resin; and
      the inner needle has the light absorbent member at a tip of the hollow tube;
   a probe for detecting the first photoacoustic waves that are generated from the needle after at least a part of the needle is inserted into the subject;
   a processing circuitry for generating a first photoacoustic image on the basis of the first photoacoustic waves;
   a second light source; and
   a second optical fiber that guides light emitted from the second light source to a light irradiation portion provided on the probe,
   wherein
   the probe further detects second photoacoustic waves that are generated in the subject due to light emitted from the second light source after the light emitted from the second light source is emitted to the subject, and
   the processing circuitry further generates a second photoacoustic image on the basis of the second photoacoustic waves.

2. The photoacoustic image generating device according to claim 1,
   wherein the first light source is a semiconductor laser light source.

3. The photoacoustic image generating device according to claim 1,
   wherein
   the probe is further capable of detecting reflected acoustic waves of acoustic waves transmitted to the subject,
   the processing circuitry is further for generating a reflected acoustic wave-image on the basis of the reflected acoustic waves.

4. The photoacoustic image generating device according to claim 3,
   wherein the processing circuitry is further for combining the first photoacoustic image, the second photoacoustic image and the reflected acoustic wave-image.

5. The photoacoustic image generating device according to claim 1,
   wherein the second light source also functions as the first light source, and
   a part of the light emitted from the second light source is branched toward the light irradiation portion provided on the probe via the second optical fiber and a part of the light emitted from the second light source is branched toward the inner needle.

* * * * *